(12) United States Patent
Ishino et al.

(10) Patent No.: US 11,046,939 B2
(45) Date of Patent: Jun. 29, 2021

(54) DNA POLYMERASE VARIANT

(71) Applicants: KYUSHU UNIVERSITY, NATIONAL UNIVERSITY CORPORATION, Fukuoka (JP); TAKARA BIO INC., Kusatsu (JP)

(72) Inventors: Yoshizumi Ishino, Fukuoka (JP); Sonoko Ishino, Fukuoka (JP); Takeshi Yamagami, Fukuoka (JP); Takashi Uemori, Otsu (JP); Nariaki Takatsu, Kusatsu (JP)

(73) Assignees: KYUSHU UNIVERSITY, NATIONAL UNIVERSITY CORPORATION, Fukuoka (JP); TAKARA BIO INC., Kusatsu (JP)

( * ) Notice: Subject to any disclaimer, the term of this patent is extended or adjusted under 35 U.S.C. 154(b) by 0 days.

(21) Appl. No.: 15/779,247

(22) PCT Filed: Nov. 24, 2016

(86) PCT No.: PCT/JP2016/084807
§ 371 (c)(1),
(2) Date: May 25, 2018

(87) PCT Pub. No.: WO2017/090684
PCT Pub. Date: Jun. 1, 2017

(65) Prior Publication Data
US 2018/0346889 A1    Dec. 6, 2018

(30) Foreign Application Priority Data
Nov. 27, 2015  (JP) ............................. JP2015-231674

(51) Int. Cl.
*C12N 9/12*  (2006.01)
*C12N 1/20*  (2006.01)
(Continued)

(52) U.S. Cl.
CPC ............. *C12N 9/1252* (2013.01); *C12N 1/20* (2013.01); *C12N 15/52* (2013.01); *C12N 15/63* (2013.01);
(Continued)

(58) Field of Classification Search
None
See application file for complete search history.

(56) References Cited

U.S. PATENT DOCUMENTS

| 6,346,379 B1 | 2/2002 | Gelfand et al. |
| 2003/0073081 A1 | 4/2003 | Mukai et al. |

(Continued)

FOREIGN PATENT DOCUMENTS

| CN | 1218832 A | 6/1999 |
| CN | 102245761 A | 11/2011 |

(Continued)

OTHER PUBLICATIONS

PIR Accession No. JX0256, published Sep. 30, 1993 (Year: 1993).*
(Continued)

*Primary Examiner* — Richard C Ekstrom
(74) *Attorney, Agent, or Firm* — Birch, Stewart, Kolasch & Birch, LLP

(57) ABSTRACT

The present invention relates to a *Thermus aquaticus* (Taq) polymerase having a strand displacement activity in which an amino acid residue in a template DNA binding site of the DNA polymerase is substituted with an amino acid to increase a total charge in the site, a nucleic acid encoding the polymerase, a vector containing the nucleic acid, a transformant containing the vector containing the nucleic acid or the nucleic acid, a method for producing the polymerase, a method for amplifying nucleic acids utilizing the polymerase, and a kit containing the polymerase. According to the present invention, a DNA polymerase having a high
(Continued)

thermostability, capable of efficiently replicating a long-strand of a template DNA, and having a strong strand displacement activity is provided.

19 Claims, 5 Drawing Sheets

Specification includes a Sequence Listing.

(51) Int. Cl.
*C12N 15/52* (2006.01)
*C12N 15/63* (2006.01)
*C12N 15/70* (2006.01)
*C12N 15/74* (2006.01)
*C12P 19/34* (2006.01)

(52) U.S. Cl.
CPC ............ *C12N 15/70* (2013.01); *C12N 15/74* (2013.01); *C12P 19/34* (2013.01)

(56) References Cited

U.S. PATENT DOCUMENTS

| | | |
|---|---|---|
| 2003/0157533 A1 | 8/2003 | Davis et al. |
| 2005/0037412 A1* | 2/2005 | Meier ................ C12N 9/1252 435/6.11 |
| 2005/0123950 A1 | 6/2005 | Mukai et al. |
| 2005/0239100 A1 | 10/2005 | Mukai et al. |
| 2005/0260606 A1 | 11/2005 | Kermekchiev et al. |
| 2011/0281305 A1 | 11/2011 | Bourn et al. |
| 2013/0022980 A1 | 1/2013 | Nelson et al. |
| 2018/0346889 A1* | 12/2018 | Ishino ................ C12N 9/1252 |

FOREIGN PATENT DOCUMENTS

| | | |
|---|---|---|
| JP | 3433929 B2 | 8/2003 |
| JP | 2005-512566 A | 5/2005 |
| JP | 2008-506417 A | 3/2008 |
| JP | 4128074 B2 | 7/2008 |
| JP | 2009-136188 A | 6/2009 |
| WO | WO 2010/091203 A2 | 8/2010 |
| WO | 2011/055737 A1 | 5/2011 |

OTHER PUBLICATIONS

UniProt Accession No. Q58I34_THEAQ, published Apr. 26, 2005 (Year: 2005).*
UniProt Accession No. B6VAI9_9DEIN, published Dec. 16, 2008 (Year: 2008).*
English translations of the Written Opinion of the International Searching Authority and International Search Report (forms PCT/ISA/237 and PCT/ISA/210), dated Feb. 21, 2017, for International Application No. PCT/JP2016/084807.
Fire et al., "Rolling Replication of Short DNA Circles," Proc. Natl, Acad. Sci. USA, Biochemistry, vol. 92, May 1995, pp. 4641-4645.
Li et al., "Crystal Structures of Open and Closed Forms of Binary and Ternary Complexes of the Large Fragment of Thermus aquaticus DNA Polymerase I: Structural Basis for Nucleotide Incorporation," The EMBO Journal, vol. 17, No. 24, 1998, pp. 7514-7525.
Nakamura et al., "Watching DNA Polymerase η Make a Phosphodiester Bond," Laboratory of Molecular Biology, vol. 53, No. 5, 2013, pp. 254-257, with English abstract.
Notomi et al., "Loop-mediated Isothermal Amplification of DNA," Nucleic Acids Research, vol. 28, No. 12, e63, 2000, pp. i-vii.
Walker et al., "Isothermal in vitro Amplification of DNA by a Restriction Enzyme/DNA Polymerase System," Proc. Natl. Acad. Sci. USA, Applied Biological Sciences, vol. 89, Jan. 1992, pp. 392-396.
Walker et al., "Strand Displacement Amplification-an Isothermal, in vitro DNA amplification Technique," Nucleic Acids Research, vol. 20, No. 7, 1992, pp. 1691-1696.
Xu et al., "Cross Priming Amplification: Mechanism and Optimization for Isothermal DNA Amplification," Scientific Reports, vol. 2, No. 246, Published Feb. 3, 2012, pp. 1-7.
Yamagami et al., "Mutant Taq DNA Polymerases with Improved Elongation Ability as a Useful Reagent for Genetic Engineering," Frontiers in Microbiology, Evolutionary and Genomic Microbiology, vol. 5, Article 461, Published Sep. 3, 2014, pp. 1-10.

* cited by examiner

[FIG. 1]
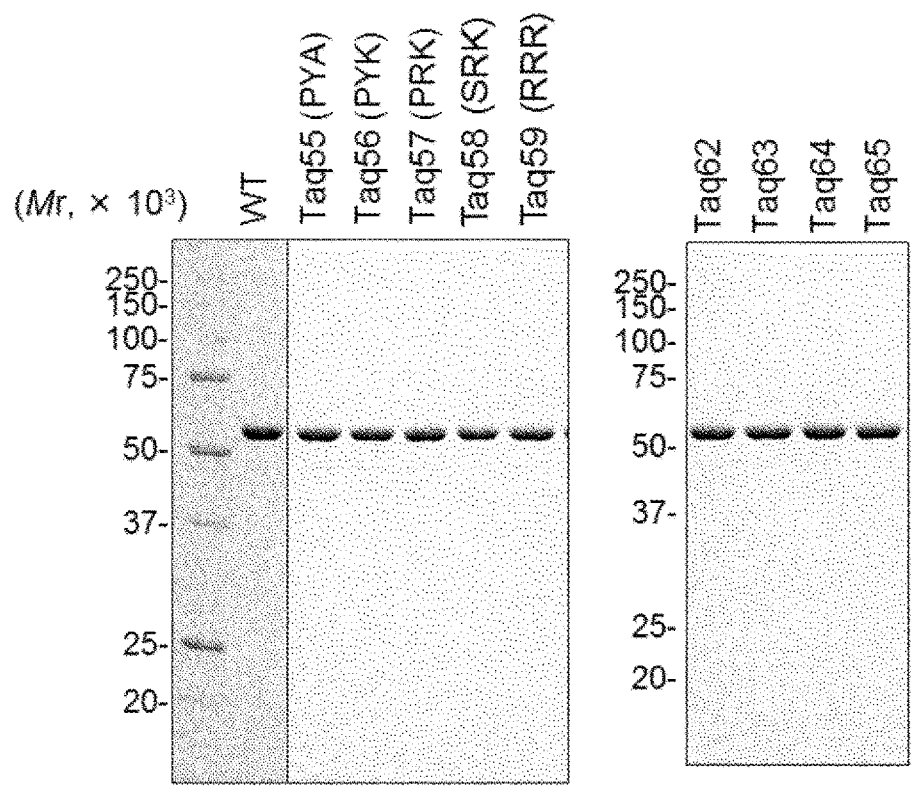

[FIG. 2-1]
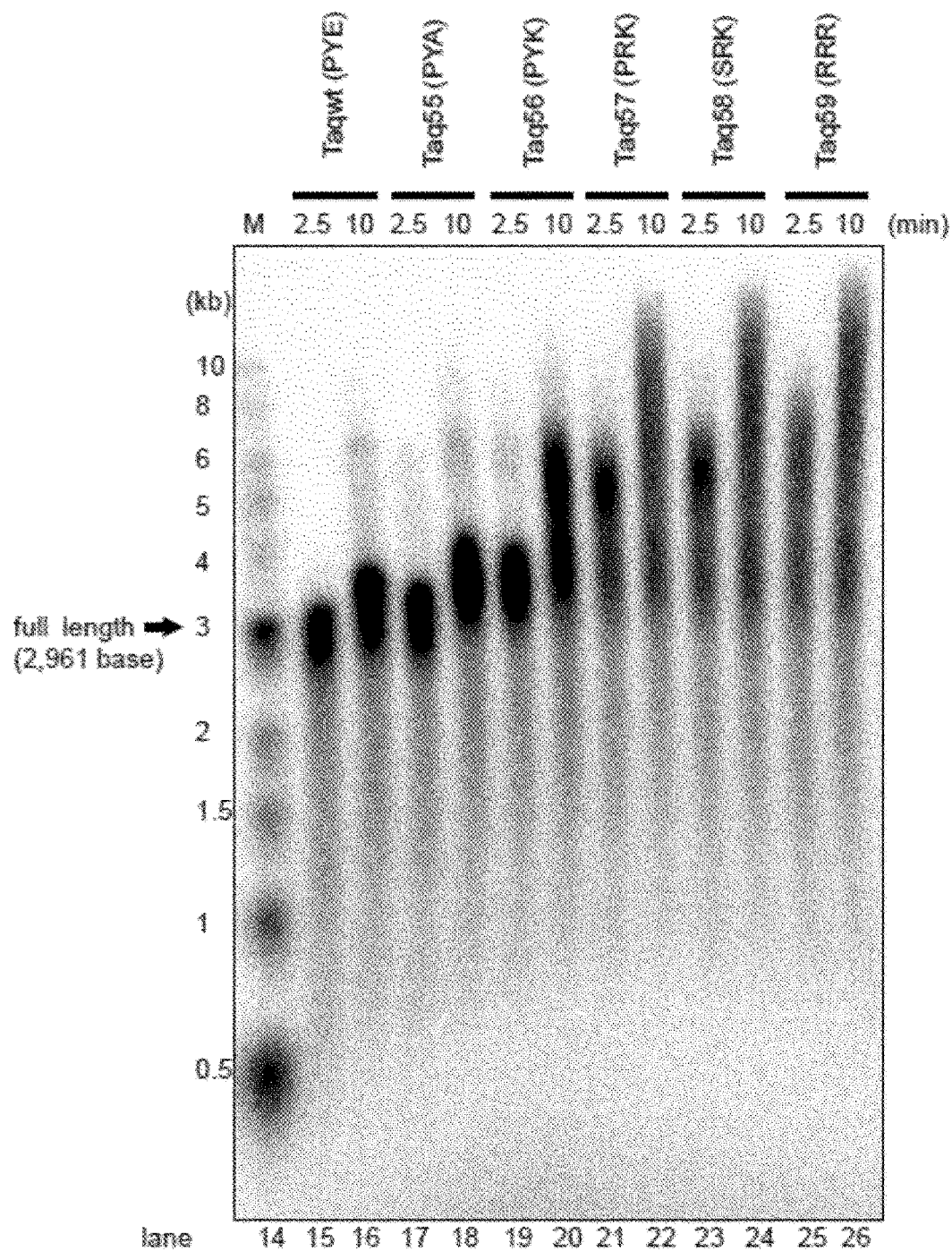

[FIG. 2-2]
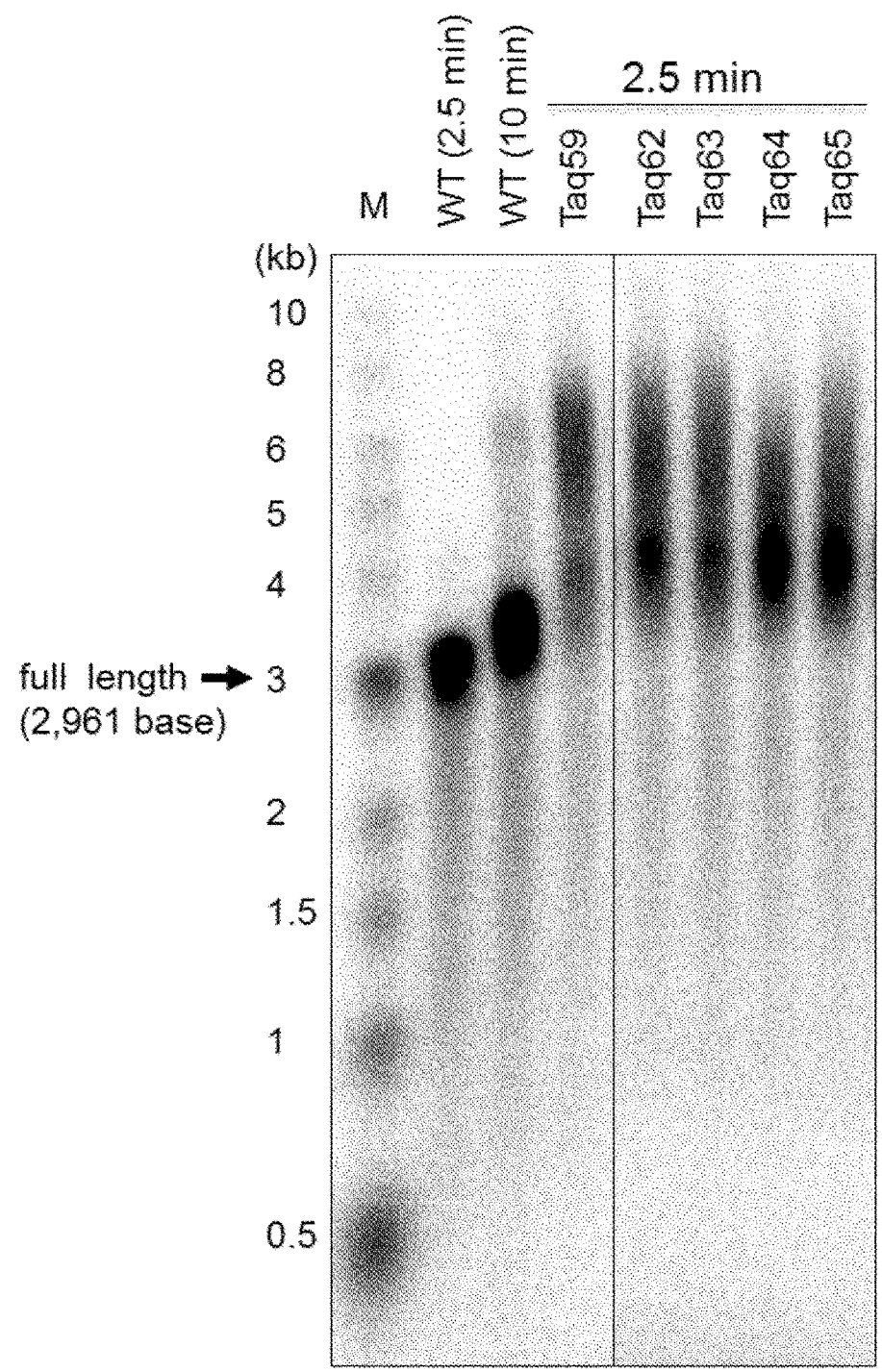

[FIG. 3]
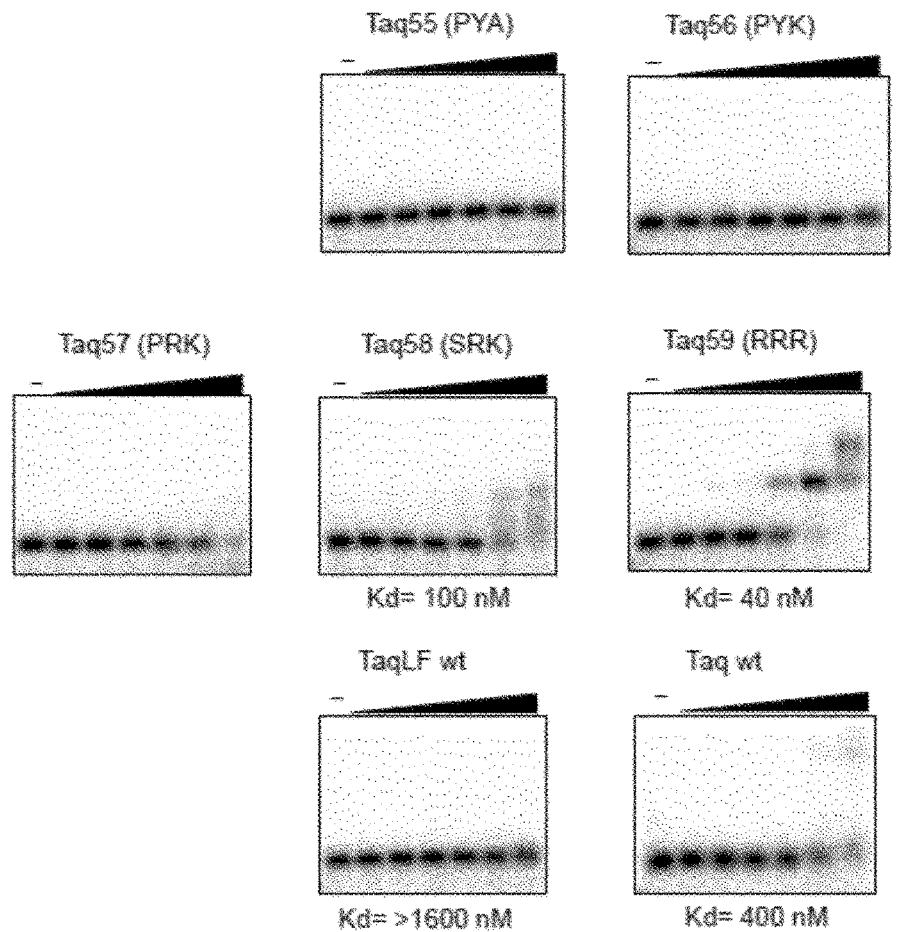
[FIG. 4]
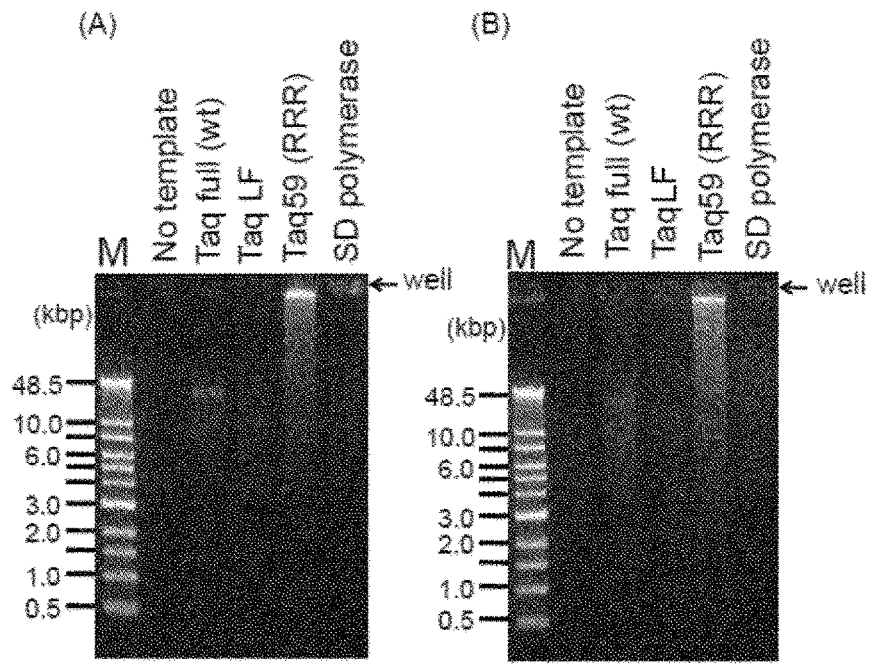

[FIG. 5]
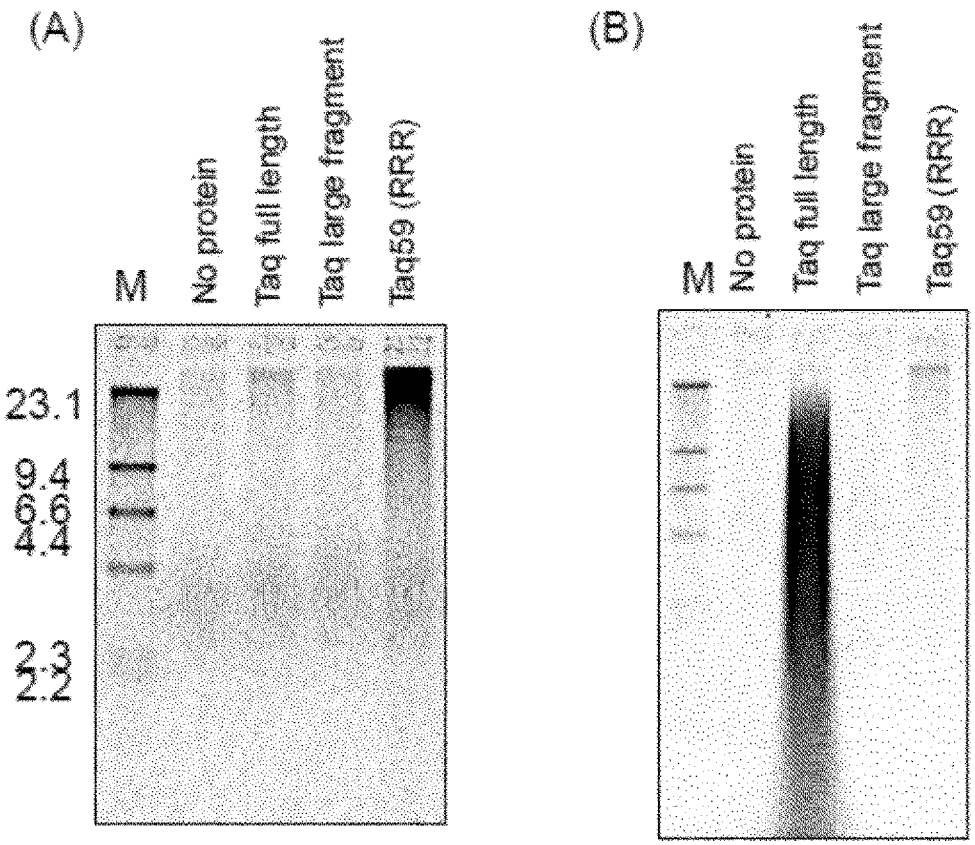
[FIG. 6]
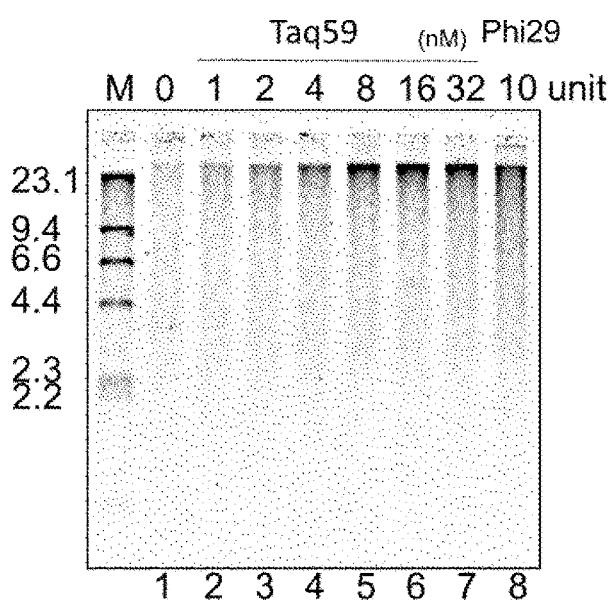

DNA POLYMERASE VARIANT

TECHNICAL FIELD

The present invention relates to a DNA polymerase variant.

BACKGROUND ART

A DNA polymerase is a useful enzyme as a reagent for genetic engineering and has been widely used in nucleic acid amplification methods, DNA sequencing, labeling of a nucleic acid, site-directed mutagenesis and the like. In addition, various DNA polymerases which are suitable for PCR method or Whole Genome Amplification (hereinafter, may also be referred to as WGA), which is one kind of nucleic acid amplification methods, have been developed and made commercially available from each company.

The DNA polymerases which have been presently known are classified into seven families (A, B, C, D, E, X, and Y) based on similarities of their amino acid sequences. Among them, DNA polymerases belonging to Family A (also referred to as Pol I-type enzyme) and Family B (also referred to as α-type enzyme) have been made commercially available as reagents for genetic engineering.

Examples of enzymes belonging to Family A include Pol I from *Thermus aquaticus* (which may be hereinafter described as Taq polymerase), Pol I from *Geobacillus stearothermophilus* (which may be hereinafter described as Bst polymerase) and Pol I from *Thermus thermophilus* (which may be hereinafter described as Tth polymerase).

Features of the DNA polymerase belonging to Family A include a strong DNA strand extension activity, many enzymes not having a 3'→5' exonuclease activity (proof-reading activity, hereinafter, also described as a 3'→5' exo activity), having a TdT (terminal deoxynucleotide transferase) activity, and the like. In addition, there are enzymes with or without a strand displacement activity, and the Taq polymerase does not have the strand displacement activity, but a large fragment of Bst polymerase has the activity. The Tth polymerase has been known as a DNA polymerase which also has a reverse transcription activity in combination.

A strand displacement activity (hereinafter, also described as to SD activity) is an activity of replicating a new DNA strand while self-dissociating hydrogen bonds of a double-stranded DNA used as a template. A strand-displacement DNA polymerase has some features that the polymerase does not necessitate the dissociation of a template double-stranded DNA from its properties, so that DNA synthesis can be performed at a constant temperature, and that it is less likely to inhibit the synthesis due to a secondary structure of the DNA.

The strand-displacement DNA polymerases have been often utilized in reactions for isothermal nucleic acid amplification. The reaction for isothermal nucleic acid amplification includes Strand-Displacement DNA extension reaction (Strand Displacement Amplification, which may be hereinafter described as SDA; Non-Patent Publications 1 and 2), Rolling Circle Amplification (which may be hereinafter described as RCA; Non-Patent Publication 3), Cross Priming Amplification (which may be hereinafter described as CPA; Non-Patent Publication 4), Loop-Mediated Isothermal Amplification (which may be hereinafter described as LAMP; Non-Patent Publication 5), ICAN (Isothermal and Chimeric primer-initiated Amplification of Nucleic acids, which may be hereinafter described as ICAN; Patent Publications 1 and 2) method, and the like.

A DNA polymerase from phi29 phage belonging to Family B (which may be hereinafter described as φ29 polymerase) has a very strong strand displacement activity. This enzyme has been utilized in carrying out replication of a template DNA in accordance with rolling circle amplification. Examples of commercially available products are TempliPhi and GenomiPhi (both manufactured by GE Healthcare).

In order to carry out a method for isothermal nucleic acid amplification at a high specificity, it is necessary to anneal primers to a template DNA in a sequence-specifically under high-temperature conditions. A Bst polymerase is a thermostable DNA polymerase having a strand displacement activity, but the polymerase has an optimal temperature of about 63° C. and is inactivated at 68° C. or higher. The φ29 polymerase has the features of showing an activity at a moderate temperature region of from 20° to 37° C. and being inactivated by heating at 65° C. for 10 minutes. Therefore, these polymerases cannot be used in a reaction for amplifying nucleic acids in which a template DNA is dissociated by thermal denaturation.

As a variant of a thermostable Taq polymerase which is provided with a strand displacement activity and lacks an exo activity, SD Polymerase (manufactured by BIORON, WO 2014/161712) has been commercially available. However, the amplification efficiency in PCR using the SD Polymerase is comparable to those of conventional Vent DNA polymerase from *Thermococcus litoralis* or Pfu polymerase from *Pyrococcus furiosus*.

Therefore, a DNA polymerase having a high thermostability, capable of efficiently replicating a long-strand of template DNA, and preferably having a strong strand displacement activity has been desired.

PRIOR ART REFERENCES

Patent Publications

Patent Publication 1: Japanese Patent Gazette No. 3433929
Patent Publication 2: Japanese Patent Gazette No. 4128074

Non-Patent Publications

Non-Patent Publication 1: *Nucleic Acids Res.*, 20(7), 1691-6, (1992)
Non-Patent Publication 2: *Proc Natl Acad Sci U.S.A.*, 89(1), 392-6, (1992)
Non-Patent Publication 3: *Proc Natl Acad Sci U.S.A.*, 92(10), 4641-5, (1995)
Non-Patent Publication 4: *Sci Rep.*, 2, 246, (2012), doi: 10.1038/srep00246
Non-Patent Publication 5: *Nucleic Acids Res.*, 28(12), E63, (2000)

SUMMARY OF THE INVENTION

Problems to be Solved by the Invention

An object of the present invention is to provide a DNA polymerase having a high thermostability, preferably having a strong strand displacement activity, and capable of efficiently replicating a long-strand template DNA.

Means to Solve the Problems

The present inventors have compared and analyzed amino acid sequences between DNA polymerases belonging to Family A. As a result, the present inventors have clarified that in a template DNA binding site of a DNA polymerase lacking a 5'→6' exonuclease activity, a DNA polymerase given with a high strand displacement activity can be produced by introducing an amino acid substitution to increase a total charge of the site, and the present invention has been perfected thereby.

Concretely, a first invention of the present invention relates to a DNA polymerase having an amino acid substitution to increase a total charge at a template DNA binding site in an amino acid sequence of a DNA polymerase belonging to Family A, and not having a 5'→3' exonuclease activity, or a DNA polymerase having a sequence identity of 95% or more to the amino acid sequence of the DNA polymerase.

In the first invention of the present invention, "an amino acid to increase a total charge" includes, for example, amino acids selected from arginine, lysine, histidine, serine and alanine.

In the first invention of the present invention, "a template DNA binding site of a DNA polymerase" includes, without intending to limit the present invention to, for example, a site containing amino acid residues corresponding to 685th to 687th amino acids of the amino acid sequence of Taq DNA polymerase shown in SEQ ID NO: 1 of the Sequence Listing.

In the first invention of the present invention, a DNA polymerase having "a substituted amino acid sequence" is, for example, a DNA polymerase having one or more substitutions selected from the group consisting of:
(1) a substitution of an amino acid corresponding to 685th proline with arginine or serine,
(2) a substitution of an amino acid corresponding to 686th tyrosine with arginine, and
(3) a substitution of an amino acid corresponding to 687th glutamic acid with arginine, lysine or alanine of the amino acid sequence of a Taq DNA polymerase. Concretely, the DNA polymerases containing an amino acid sequence shown in any one of SEQ ID NOs: 40 to 48 of the Sequence Listing are included.

In the first invention of the present invention, the "DNA polymerase belonging to Family A" is preferably a thermostable DNA polymerase.

Also, in the first invention of the present invention, the "DNA polymerase belonging to Family A" may be a DNA polymerase derived from bacteria of the genus *Thermus*.

Further, in the first invention of the present invention, the "DNA polymerase belonging to Family A" is preferably a DNA polymerase having deletion of an N-terminal region as compared to an amino acid sequence of a wild-type DNA polymerase belonging to Family A, which includes, but not particularly limited to, a Taq DNA polymerase having deletion of an N-terminal region, preferably a Taq DNA polymerase having deletion of 289 amino acid residues from the N-terminus, and a Taq DNA polymerase having deletion of 280 amino acid residues from the N-terminus. In the specification, as a DNA polymerase belonging to Family A, a DNA polymerase having deletion of an N-terminal region associated with a 5'→3' exonuclease activity of a DNA polymerase belonging to a wild-type Family A is also a preferred example.

A second invention of the present invention relates to a nucleic acid containing a nucleotide sequence encoding a DNA polymerase of a first invention of the present invention. An example of the nucleic acid includes, but not particularly limited to, a nucleic acid encoding a DNA polymerase of a first invention mentioned above, the nucleic acid containing a nucleotide sequence shown in any one of SEQ ID NOs: 5 to 9 and 20 to 23 of the Sequence Listing. It is preferable that the DNA polymerase has a strand displacement activity.

A third invention of the present invention relates to a vector containing a nucleic acid encoding a DNA polymerase of a second invention of the present invention. It is preferable that the DNA polymerase has a strand displacement activity.

A fourth invention of the present invention relates to a transformant containing a vector of a third invention of the present invention, or a nucleic acid of a second invention of the present invention.

A fifth invention of the present invention relates to a method for producing a DNA polymerase, characterized by culturing a transformant of a fourth invention of the present invention, and harvesting a DNA polymerase from the cultured cells. It is preferable that the DNA polymerase has a strand displacement activity.

A sixth invention of the present invention relates to a method for producing a DNA molecule, including incubating a DNA polymerase of a first invention of the present invention together with a template DNA. In the sixth invention of the present invention, the method for producing a DNA molecule may be a polymerase chain reaction or a reaction for isothermal nucleic acid amplification. It is preferable that the DNA polymerase has a strand displacement activity.

A seventh invention of the present invention relates to a kit containing a DNA polymerase of a first invention of the present invention. It is preferable that the DNA polymerase has a strand displacement activity.

Effects of the Invention

According to the present invention, a DNA polymerase having a high thermostability, capable of efficiently replicating a long-strand of a template DNA, and preferably having a strong strand displacement activity is provided.

BRIEF DESCRIPTION OF THE DRAWINGS

FIG. 1 It is results of SDS-PAGEs of purified DNA polymerases.
FIG. 2-1 It is results of primer extension activities.
FIG. 2-2 It is results of primer extension activities.
FIG. 3 It is results of gel shift assays.
FIG. 4 It is results of agarose gel electrophoresis.
FIG. 5 It is results of alkaline agarose gel electrophoreses.
FIG. 6 It is results of alkaline agarose gel electrophoreses.

MODES FOR CARRYING OUT THE INVENTION

In the present invention, the term "strand displacement activity" refers to an activity for replicating a new DNA strand while self-dissociating hydrogen bonds of a double-stranded DNA used as a template. A preferred DNA polymerase of the present invention has a strand displacement activity, and has, for example, a strand displacement activity of the same level or stronger than those of a known DNA polymerase which has been known to have a strand displacement activity.

In the present invention, the phrase "increase a total charge" refers to a matter that a total charge of each of the amino acid residues after substitution at a given site is larger than a total charge of each of the amino acid residues before substitution at the site. Although it is not intended to limit the present invention thereto, for example, in a case of an amino acid sequence before substitution having proline-tyrosine-glutamic acid (three residues), a total charge is 0+0+(−1)=−1. If this amino acid sequence is substituted with arginine-arginine-arginine, the total charge is (+1)+(+1)+(+1)=+3. In this substitution, the total charge at the site is changed from −1 to +3, so that it is said that the total charge is increased.

The details will be given hereinbelow.

1. DNA Polymerase of the Present Invention and Nucleic Acids Encoding Same

The first embodiment of the present invention relates to a DNA polymerase, and this is a DNA polymerase having an amino acid substitution to increase a total charge at a template DNA binding site in an amino acid sequence of a DNA polymerase belonging to Family A and not having a 5'→3' exonuclease activity, and a DNA polymerase having a sequence identity of 95% or more to the above amino acid sequence of the DNA polymerase and having an activity of the same level. It is preferable that the DNA polymerase has a strand displacement activity. Here, the term "sequence identity" as used herein refers to a sequence identity in a case where an amino acid sequence other than the template DNA binding site is assumed to be 100% in the amino acid sequence of the DNA polymerase, and the DNA polymerase has a sequence identity of preferably 95% or more, and more preferably 100% to an amino acid sequence of a DNA polymerase.

In a preferred aspect of the first embodiment of the present invention, the DNA polymerase may have a total charge at the template DNA binding site increased by an amino acid substitution, and an amino acid residue of which charge at the site before and after the substitution is unchanged and an amino acid residue of which charge is increased may be present in a mixture. The increase in the total charge is achieved by substitution of from an amino acid having a negative charge to an amino acid without a charge or an amino acid having a positive charge, and substitution of from an amino acid without a charge to an amino acid having a positive charge. In the present invention, a DNA polymerase having a larger number of amino acid residues with increased charge is preferred than the number of amino acid residues without a charge, and a DNA polymerase with increased charges in all the amino acid residues at the site is more preferred. For example, a DNA polymerase in which all the amino acid residues at the site are substituted with a basic amino acid having a positive charge, and further a DNA polymerase in which all the amino acid residues at the site are substituted with arginine having the highest charge are preferred in the present invention.

As a template DNA binding site of the DNA polymerase belonging to Family A, a site binding to a template DNA may be selected from a conformation of the polymerase. For example, in a Taq polymerase shown in SEQ ID NO: 1 of the Sequence Listing, the template DNA binding site can be specified as a site containing an amino acid residue corresponding to 685th to 687th amino acids in the amino acid sequence of the polymerase, without particularly being limited thereto.

In a preferred aspect of the first embodiment of the present invention, the substituted amino acid sequence is, for example, a DNA polymerase having one or more substitutions selected from the group consisting of:

(1) a substitution of from an amino acid corresponding to 685th proline to arginine or serine,
(2) a substitution of from an amino acid corresponding to 686th tyrosine to arginine, and
(3) a substitution of from an amino acid corresponding to 687th glutamic acid to arginine, lysine or alanine, in the amino acid sequence of a wild-type Taq DNA polymerase, and preferably having a strand displacement activity.

The DNA polymerase of the present invention has the feature of not having a 5'→3' exonuclease activity. Many of the DNA polymerases belonging to Family A have a 5'→3' exonuclease activity, but it is possible to be utilized in the present invention by deleting the activity in accordance with a known method. For example, transduction of a mutation such as substitution or deletion an amino acid residue contributing to a 5'→3' exonuclease activity, or a method of deleting a domain important for the above activity has been known.

It is desired that the DNA polymerase of the present invention is a polymerase having thermostability, but not particularly limiting the present invention thereto. A thermostable DNA polymerase can be used in a reaction under high-temperature conditions, which in turn can weaken a base pair bond of DNA, is advantageous not only, needless to say, in a PCR method including thermally denaturing a DNA, but also in a method for isothermal nucleic acid amplification. The DNA polymerase of the present invention produced by utilizing a DNA polymerase of thermophilic microorganisms belonging to Family A is a particularly preferred embodiment. The term having thermostability as used herein refers to, but not particularly being limited to, for example, a property in which a residual activity is 100% when a DNA polymerase is held at 90° C. for 30 minutes, or a residual activity is 75% or more when held at 95° C. for 30 minutes.

In a Taq DNA polymerase or other thermostable DNA polymerases derived from bacteria of the genus *Thermus* (for example, *Thermus thermophilus*, *Thermus flavus*, and the like), a 5'→3' exonuclease activity domain is located at an N-terminal region, so that the DNA polymerase of the present invention can be produced by introducing the above amino acid substitutions into template DNA binding sites of N-terminal deletion products of the DNA polymerases. For example, a Taq DNA polymerase having deletion of 280 amino acid residues from the N-terminus-(KlenTaq) and a Taq DNA polymerase having deletion of 289 amino acid residues from the N-terminus-(Taq large fragment) which are described in Examples of this specification are preferred for the present invention. For example, a DNA polymerase containing an amino acid sequence selected from SEQ ID NOs: 40 to 48 of the Sequence Listing, and preferably having a strand displacement activity is included as the DNA polymerase of the present invention (concretely, a DNA polymerase variant). A DNA polymerase having an amino acid sequence shown in SEQ ID NO: 44 of the Sequence Listing is particularly preferable as the DNA polymerase of the present invention. Further, in another embodiment of the present invention, a 5'→3' exonuclease deletion product in which 117th glutamic acid residue is substituted with alanine residue, 119th aspartic acid residue is substituted with alanine residue, 142nd aspartic acid residue is substituted with alanine residue, or further 144th aspartic acid residue is substituted with alanine residue in a Taq DNA polymerase may be combined with the present invention.

In a more preferred aspect of the first embodiment of the present invention, amino acid substitutions other than those mentioned above may be further introduced, for the purpose of enhancing the properties of the DNA polymerase of the present invention. For example, a mutation described in Japanese Patent Gazette No. 4193997 (a mutation to increase a sum of charge of 742nd glutamic acid and 743rd alanine at a position of Taq polymerase) may be introduced into the DNA polymerase of the present invention, without intending to limit the present invention thereto. It has been disclosed that a DNA polymerase variant described in Japanese Patent Gazette No. 4193997 is disclosed to have an elevated extension activity, so that it can be expected that the extension activity of the DNA polymerase of the present invention is further enhanced by further transducing the mutation.

Alternatively, in the first embodiment of the present invention, the polymerase may be a DNA polymerase which is fused with a molecule having certain functions, for the purpose of enhancing the properties of the DNA polymerase. Examples of "molecule having certain functions" mentioned above include a peptide or a polypeptide having affinity to a DNA, or a peptide or a polypeptide interacting with proteins involved in synthesis of DNA. The phrase "DNA polymerase which is fused with a molecule having certain functions" as used herein may be called as "fusion polypeptide," and the fusion polypeptide is also encompassed in a DNA polymerase.

A PCNA (proliferating cell nuclear antigen) is a homopolymer that forms a cyclic structure called as "sliding clamp," which accelerates a DNA synthesis reaction. The PCNA is highly conserved from yeasts to human, and in eukaryotic cells, the PCNA plays an important role in cell divisions, DNA replications, repairs, cell cycle regulations, or post-replication modifications such as DNA methylation and chromatin remodeling. The PCNA forms a complex with various proteins other than a DNA polymerase or RFC (replication factor C), and involved in the repair or replication of DNA, or other gene controlling functions. It has been known that in human, at least twelve proteins are bound to the PCNA. Each of the proteins is bound to the PCNA via a PIP box (PCNA interaction protein box), so that the protein would be detained on a DNA strand.

Many of DNA polymerases belonging to Family A do not interact with a PCNA. However, a reaction rate or an extension ability in a DNA synthesis reaction can be improved by adding a PCNA-bindable peptide to the DNA polymerase of the present invention.

The phrase "PCNA-bindable peptide" is not particularly limited, so long as the peptides have the abilities of binding to a PCNA. Examples of the peptide include peptides containing a PIP box, which are peptides existing in various PCNA-bindable proteins. The PIP box is an amino acid sequence existing in a protein interacting with a PCNA, which serves to detain the protein on the DNA strand via the PCNA. It has been known that proteins (for example, replication factor C large subunit, etc.), which are involved in DNA replications or the like, in thermophilic bacteria have a PIP box. In the present invention, examples of a preferred PIP box include an oligopeptide composed of at least eight amino acids, denoted by A1-A2-A3-A4-A5-A6-A7-A8, wherein A1 is glutamine residue, each of A2 and A3 is any amino acid residues, A4 is an amino acid residue selected from the group consisting of leucine residue, isoleucine residue, and methionine residue, each of A5 and A6 is any amino acid residues, A7 is phenylalanine residue or tryptophan residue, and A8 is an amino acid residue selected from the group consisting of phenylalanine residue, tryptophan residue, or leucine residue. Especially preferred one includes one shown in SEQ ID NO: 52 of the Sequence Listing including eight amino acids QATLFDFL. Further, in the present invention, the peptide may be an oligopeptide containing 9 amino acids in which the above oligopeptide of eight amino acids further contains lysine residue at an N-terminus side thereof.

Further, the PIP box used in the present invention includes those derived from thermophilic bacteria-producing proteins, but not particularly limited thereto. Examples include preferably a PIP box derived from a replication factor C large subunit of thermophilic bacteria, and more preferably a PIP box derived from a replication factor C large subunit of *Pyrococcus furiosus*. Alternatively, it may be a functional equivalent having substantially same level of activity as those mentioned above.

In addition, these PIP boxes may exist in plurality within a fusion polypeptide of the present invention. Examples of the number of PIP boxes contained in the fusion polypeptide include, but not particularly limited to from 1 to 6, and preferably from 2 to 4. These plural PIP boxes may each have amino acid sequences different from each other, so long as they play their roles. In addition, between the plural PIP boxes themselves, for example, other amino acid sequences, for example, a linker peptide mentioned later may be inserted.

Further, a "linker peptide" may be present at a C-terminal side of the above PIP box. The term "linker peptide" constituting the fusion polypeptide of the present invention refers to a peptide which is inserted between polypeptides that are fused together or between a peptide and a polypeptide in the fusion polypeptide of the present invention in order to avoid the inhibition of their functions or folding. The length of the linker peptide includes, but not particularly limited to, peptides of from 3 to 100 amino acids, preferably 5 to 50 amino acids. The kinds of the amino acids constituting the linker peptide are not particularly limited, and it is better to avoid a linker which itself forms a complicated conformation, and a peptide richly containing an amino acid having a relative small side chain, for example, serine or glycine, is well used.

The DNA polymerase of the present invention in which the above PIP box is added at an N-terminal region is preferred, without intending to limit the present invention thereto. When the DNA polymerase of the present invention in which the above PIP box is added at an N-terminal region is used, a liquid reaction mixture containing a PCNA is used, without intending to limit the present invention thereto. As the PCNA mentioned above, a known PCNA or a variant thereof can be used, and preferably a thermostable PCNA or a variant thereof is used. Examples are, but not particularly limited to, PCNA from *Pyrococcus furiosus* or PCNA from *Thermococcus kodakarensis*, and the like. Further, a variant PCNA can be also used in various embodiments of the present invention including a composition for amplifying nucleic acids of the present invention and the like. Examples of preferred variant PCNAs which can be used in the present invention are a variant PCNA described in WO 2007/004654, concretely variant PCNAs having sequence in which a 82nd, 84th, 109th, 139th, 143rd or 147th amino acid residue of a PCNA from *P. furiosus* is substituted with another amino acid. In an especially preferred embodiment of the present invention, an example is a variant PCNA having a sequence in which a 143rd amino acid residue aspartic acid is substituted with arginine (D143R).

The second embodiment of the present invention is a nucleic acid encoding a DNA polymerase of a first embodiment of the present invention. Preferably, the nucleic acid may be a nucleic acid encoding a DNA polymerase containing an amino acid sequence selected from SEQ ID NOs: 40 to 48 of the Sequence Listing. More preferably, the nucleic acid is a nucleic acid containing a nucleotide sequence selected from SEQ ID NOs: 5 to 9 and 20 to 23 of the Sequence Listing. Especially preferably, the nucleic acid is a nucleic acid containing the nucleotide sequence shown in SEQ ID NO: 9 of the Sequence Listing. It is preferable that the DNA polymerase has a strand displacement activity.

The nucleic acid encoding a DNA polymerase of a first embodiment of the present invention is not particularly limited, so long as the nucleic acid is a codon encoding a protein is expressible in a host to be used and has a DNA polymerase activity, and the codon may be optimized to make it expressible or increase its expression level. It is preferable that the optimization is carried out in accordance with methods ordinarily used in the art. Incidentally, when the optimization of codon is carried out, it is necessary not to cause an alteration in an amino acid sequence which is encoded.

The nucleic acid of a second embodiment of the present invention may further contain a nucleic acid encoding an affinity tag in order to facilitate purification of a polypeptide expressed. The nucleic acid of the second embodiment of the present invention is, for example, a nucleic acid encoding histidine (His) tag, a glutathione S-transferase (GST) tag, a maltose binding protein (MBP) tag, a Strep(II) tag consisting of eight amino acid residues (Trp-Ser-His-Pro-Gln-Phe-Glu-Lys), or the like, without intending to limit the present invention thereto. The position at which the tag is added may be either one of a 5'-terminal side and/or a 3'-terminal side of a nucleic acid encoding a DNA polymerase of the present invention, and the tag may be properly added at a position that would not be a hindrance to expression and tag functions. Here, it is preferable that the tag is a tag which can be cleaved in the purification stage of the expressed fusion protein. The cleavable tag is, for example, a tag containing a nucleic acid encoding a recognition sequence of a protease for cleaving a fusion polypeptide such as Facror Xa, Pre-Scission Protease, Thrombin, enterokinase, or TEV protease (Tobacco Etch Virus Protease), without intending to limit the present invention thereto.

The third embodiment of the present invention is a vector containing a nucleic acid of a second embodiment of the present invention. The vector for inserting a nucleic acid of a second embodiment of the present invention is not particularly limited, so long as the vector is an expression vector which is ordinarily used in the art. A vector capable of self-replication in a host cell or a vector capable of being incorporated into a host chromosome can be used. As the vector mentioned above, for example, a plasmid vector, a phage vector, a virus vector or the like can be used. As the plasmid vector, a plasmid which is suitable for a host to be used, for example, a plasmid derived from *Escherichia coli*, a plasmid derived from bacteria of the genus *Bacillus*, and a plasmid derived from yeasts are well known to a person skilled in the art, and many of them are commercially available. In the present invention, these known plasmids or modified forms thereof can be used. As the phage vector, for example, a λ phage (e.g., Charon4A, Charon21A, EMBL3, EMBL4, λgt10, λgt11, λZAP) or the like can be used, and as the virus vector, for example, an animal virus such as a retrovirus or a vaccinia virus, or an insect virus such as a baculovirus can be used. A promoter which is carried on an expression vector can be selected depending upon a host, and, for example, in *Escherichia coli*, a promoter derived from *Escherichia coli*, a phage or the like, such as a trp promoter, a lac promoter, a PL promoter, or a PR promoter, or a modified product thereof can be used, without intending to limit to those mentioned above. Further, an expression system (e.g., pET expression system, etc.) in which a promoter derived from a phage and an RNA polymerase gene are combined may be utilized. Further, a heterologous protein expression system in which an yeast, an insect cell or a mammalian cell is used as a host has been numerously constructed, and has already been commercially available. In the production of the DNA polymerase such as the fusion polypeptide of the present invention, these expression systems may be used.

The fourth embodiment of the present invention is a transformant containing a vector of a third embodiment of the present invention or a nucleic acid of a second embodiment of the present invention. A host which is transformed with a vector of a third embodiment of the present invention or a host into which a nucleic acid of a second embodiment of the present invention is introduced is not particularly limited, so long as the host is a host which is ordinarily used in the art. As host cells, any one of prokaryotic cells, yeasts, animal cells, insect cells, plant cells, and the like may be used so long as the host is capable of expressing the DNA polymerase such as the fusion polypeptide of the present invention.

When a prokaryotic cell is used as a host cell, for example, bacteria belonging to the genus *Escherichia* such as *Escherichia coli*, bacteria belonging to the genus *Bacillus* such as *Bacillus subtilis*, bacteria belonging to the genus *Pseudomonas* such as *Pseudomonas putida*, bacteria belonging to the genus *Rhizobium* such as *Rhizobium meliloti* can be used as host cells. *Escherichia coli* which can be used in the production of heterologous proteins is well known to a person skilled in the art, and many of them are commercially available (e.g., *Escherichia coli* BL21, *E. coli* XL 1-Blue, *E. coli* XL2-Blue, *E. coli* DH1, *E. coli* JM109, *E. coli* HB101, etc.). Also, *Bacillus subtilis* MI114, *B. subtilis* 207-21 or the like, which is a bacterium of the genus *Bacillus*, or *Brevibacillus choshinensis* or the like, which is a bacterium of the genus *Brevibacillus*, has been known as a host for production of heterologous protein. These host cells can be combined with an appropriate expression vector and used in the production of the DNA polymerase such as the fusion polypeptide of the present invention.

The method for introducing an expression vector into a host is not particularly limited, so long as the method is capable of introducing a nucleic acid into a host, and, for example, a method using calcium ions, an electroporation method, a spheroplast method, a lithium acetate method or the like can be used. The method for introducing a recombinant vector into an insect cell is not particularly limited, so long as the method is capable of introducing a DNA into an insect cell, and, for example, a calcium phosphate method, a lipofection method, an electroporation method, or the like can be used. The infection of a phage vector or a virus vector to a host cell is carried out in accordance with a method depending on these vectors, whereby a transformant which expresses the DNA polymerase such as the fusion polypeptide of the present invention can be obtained.

The fifth embodiment of the present invention is a method for producing a DNA polymerase, characterized by culturing a transformant of a fourth embodiment of the present invention, and harvesting a DNA polymerase from the cultured cells. It is preferable that the DNA polymerase has a strand displacement activity. The culture conditions are not particularly limited, so long as the culture conditions are suitable for an expression vector, a host or the like to be used. Although it is not intended to limit the present invention thereto, for example, when *Escherichia coli* is transformed with a pET vector, a transformant is inoculated to an LB medium, and the transformant is subjected to shaking culture, for example, at 37° C. At a point where an OD of a culture solution reaches 0.2 to 0.3, IPTG is added thereto. In order to induce expression of an intended protein, the mixture is subjected to shaking culture, for example, at 37° C. for 2 to 5 hours, or in a case where an expression level is low at 37° C., the mixture is subjected to shaking culture at 15° to 30° C. for 2 to 24 hours, and preferably at 20° to 25° C. for 4 to 5 hours, or preferably at 20° to 25° C. for 10 to 20 hours, for the purpose of further increasing an expression level. The culture broth is centrifuged, the obtained bacterial cells are washed, and thereafter the washed product is subjected to ultrasonic disruption, whereby a DNA polymerase of the present invention can be obtained. Since the disruption contains contaminants in a large amount, it is desired that a purification method used in the art is carried out, for example, purification including appropriately combining ammonium sulfate precipitation method, anion exchange column, cation exchange column, gel filtration column, affinity chromatography column, dialysis, and the like.

2. Method for Amplifying Nucleic Acids Using DNA Polymerase of the Present Invention A method for amplifying nucleic acids using the DNA polymerase of the present invention can be utilized in the production of a DNA molecule. An example of the above method for amplifying nucleic acids of the present invention is a method for producing a DNA molecule, including incubating a DNA polymerase of the present invention together with a template DNA, without intending to limit the present invention thereto. Here, it is preferable that the DNA polymerase has a strand displacement activity. The method may further contain a primer. The primer may be one or plural members. In addition, the primer may be a specific primer, a random primer, or a mixture thereof. The kinds of the primer can be appropriately selected depending on the purpose. The method for producing the DNA molecule may be a method which is ordinarily used in the art. The above method for amplifying nucleic acids of the present invention can be used in, for example, a polymerase chain reaction or a reaction for isothermal nucleic acid amplification, without intending to limit the present invention thereto.

When a reaction utilizing the DNA polymerase of the present invention is carried out, a liquid reaction mixture usually containing a divalent metal salt (a magnesium salt, etc.), dNTP (deoxyribonucleotide triphosphate), a buffering component for maintaining a pH, and the like is prepared. Examples of the divalent metal ions constituting the divalent metal salt include magnesium ions, manganese ions, and cobalt ions. The divalent metal ions that are suitable for each of the DNA polymerases and concentrations thereof have been known in the art. The divalent metal ions can be supplied in the form of salts such as chlorides, sulfates, or acetates. Examples of the divalent metal ion concentration in the composition of the present invention are, for example, from 0.5 to 20 mM without particularly limiting the present invention thereto. At least one member of dATP, dCTP, dGTP, and dTTP or derivatives thereof is used as the dNTP. Preferably, a mixture of four kinds of dATP, dCTP, dGTP, and dTTP is used.

When DNA synthesis is carried out using primers, an oligonucleotide having a sequence complementary to a nucleotide sequence of a nucleic acid used as a template and hybridizing to a nucleic acid which serves as a template in the used reaction conditions is used as a primer. The strand length of the primer is preferably 6 nucleotides or more, and more preferably 10 nucleotides or more, from the viewpoint of specificity of hybridization, and the strand length is preferably 100 nucleotides or less, and more preferably 30 nucleotides or less, from the viewpoint of synthesis of the oligonucleotide. The above oligonucleotide can be chemically synthesized, for example, by a known method. In addition, the oligonucleotide may be an oligonucleotide derived from an organism sample, and, for example, an oligonucleotide may be prepared by isolating from a restriction endonuclease digest of a DNA prepared from a natural sample.

The DNA polymerase of the present invention is particularly useful in DNA synthesis under isothermal conditions with a double-strand nucleic acid as a template, because the polymerase has an excellent strand displacement activity. As mentioned in the following Example 3, a DNA having a long-strand length can be synthesized under isothermal conditions with a microbial genomic DNA as a template. The DNA having a long-strand length is useful as a DNA for genome analysis or genome editing.

Furthermore, the method for amplifying nucleic acids of the present invention may be combined with a real-time detection technique. In the real-time detection, an amplified product is detected with the passage of time, concurrently with the amplification reaction using an intercalator or a fluorescent-labeled probe. The intercalator includes SYBR (registered trademark) Green I and other nucleic acid-binding dye, and the fluorescent-labeled probe includes CyCleave(registered trademark) probe, or molecular beacon probe, and the like, respectively.

3. Kit of Present Invention

The kit of the present invention is a kit containing a DNA polymerase of the present invention. Here, it is preferable that the DNA polymerase has a strand displacement activity. The kit may further contain, in addition to the DNA polymerase of the present invention a primer used in the above reaction, reagents needed for the reaction such as a divalent metal salt, dNTP, a buffer or sterile water, a natural or artificial template DNA for a positive control, and a sterilized tube which is a container, without intending to limit the present invention thereto. Further, a kit containing a composition which can be used only by mixing a DNA polymerase of the present invention, a divalent metal salt, dNTP, a buffer component, and the like, and adding a template DNA and water (sterile water, etc.) upon use is also encompassed in the present invention.

Further, the kit of the present invention may contain an intercalator or fluorescent-labeled probe. The intercalator includes SYBR(registered trademark) Green I and other nucleic acid-binding dye, and the fluorescent-labeled probe includes CyCleave(registered trademark) probe, or molecular beacon probe, and the like, respectively.

EXAMPLES

The present invention will be more particularly described hereinbelow by illustrative Examples, without intending to limit the scope of the present invention to these Examples.

Example 1

Preparation of Taq Polymerase Having SD Activity (1) Preparation of Polymerase Variant Plasmid A region of from P685 to E687 in an amino acid sequence of a Taq polymerase (GenBank No.: AAA27507) was remarked and variants listed below were prepared. Concretely, a pET24a plasmid (manufactured by Merck Millipore) having insertion of a Taq large fragment having a nucleotide sequence shown in SEQ ID NO: 4 of the Sequence Listing (Taq DNA polymerase having deletion of 289 amino acid residues from an N-terminus; which may be hereinafter expressed as TaqLF) was prepared. The plasmid is called pET-TaqLF plasmid. A site-directed mutation was introduced based on this plasmid using QuickChange site-directed mutagenesis kit (manufactured by Agilent Biotechnologies).

In addition, in Taq55 to Taq59 variants, a site-directed mutation was carried out with a combination of a primer set for mutagenesis listed in Table 1, with the pET-TaqLF plasmid mentioned above as a template DNA. The conditions for PCR at the time of preparation were such that 14 cycles of reaction were carried out, wherein one cycle is 95° C. for 30 seconds, 55° C. for 60 seconds, and 68° C. for 8 minutes. After the termination of the reaction, E. coli JM109 strain (manufactured by TAKARA BIO INC.) was transformed with 1 µl of a liquid reaction mixture, and the transformants were spread on an LB-kanamycin plate. Plasmids were purified from the colonies formed, and nucleotide sequences were analyzed to confirm that intended sequences were obtained.

TABLE 1

| # | Name of Variant | Position of Mutation | Primer 1 | Primer 2 |
|---|---|---|---|---|
| 1 | Taq55 (SEQ ID NO: 5) | E687A | TaqPYA-5 (SEQ ID NO: 10) | TaqPYA-3 (SEQ ID NO: 11) |
| 2 | Taq56 (SEQ ID NO: 6) | E687K | TaqPYK-5 (SEQ ID NO: 12) | TaqPYK-3 (SEQ ID NO: 13) |
| 3 | Taq57 (SEQ ID NO: 7) | Y686R, E687K | TaqPRK-5 (SEQ ID NO: 14) | TaqPRK-3 (SEQ ID NO: 15) |
| 4 | Taq58 (SEQ ID NO: 8) | P685S, Y686R, E687K | TaqSRK-5 (SEQ ID NO: 16) | TaqSRK-3 (SEQ ID NO: 17) |
| 5 | Taq59 (SEQ ID NO: 9) | P685R, Y686R, E687R | TaqRRR-5 (SEQ ID NO: 18) | TaqRRR-3 (SEQ ID NO: 19) |

Further, Taq62 to Taq65 variants were prepared based on the Taq59 variant. Concretely, in the Taq62 variant, a site-directed mutation was carried out three times, with a primer set for mutagenesis of a combination of SEQ ID NOs: 24 and 25, a combination of SEQ ID NOs: 26 and 27, or a combination of SEQ ID NOs: 28 and 29 listed in Table 2, with pET28-TaqLF plasmid described in Example 1(1) as a template DNA. Also, in Taq63 to Taq65 variants, a site-directed mutation was carried out with a primer set for mutagenesis listed in Table 2 in the same manner as in Taq62. The mutagenesis and purification are the same as the above-mentioned procedures.

TABLE 2

| # | Name of Variant | Position of Mutation | Primer 1 | Primer 2 |
|---|---|---|---|---|
| 6 | Taq62 (SEQ ID NO: 20) | H676Y, P685R, Y686R, E687R, E742A | TaqAYR-5 (SEQ ID NO: 24) TaqRRR-5 (SEQ ID NO: 26) aa5 (SEQ ID NO: 28) | TaqAYR-3 (SEQ ID NO: 25) TaqRRR-3 (SEQ ID NO: 27) aa3 (SEQ ID NO: 29) |
| 7 | Taq63 (SEQ ID NO: 21) | H676Y, P685R, Y686R, E687R, E742H | TaqAYR-5 (SEQ ID NO: 30) TaqRRR-5 (SEQ ID NO: 32) ha5 (SEQ ID NO: 34) | TaqAYR-3 (SEQ ID NO: 31) TaqRRR-3 (SEQ ID NO: 33) ha3 (SEQ ID NO: 35) |

TABLE 2-continued

| # | Name of Variant | Position of Mutation | Primer 1 | Primer 2 |
|---|---|---|---|---|
| 8 | Taq64 (SEQ ID NO: 22) | H676Y, P685R, Y686R, E687R, E742H, A743K | TaqAYR-5 (SEQ ID NO: 30) TaqRRR-5 (SEQ ID NO: 32) hk5 (SEQ ID NO: 36) | TaqAYR-3 (SEQ ID NO: 31) TaqRRR-3 (SEQ ID NO: 33) hk3 (SEQ ID NO: 37) |
| 9 | Taq65 (SEQ ID NO: 23) | H676Y, P685R, Y686R, E687R, E742R, A743R | TaqAYR-5 (SEQ ID NO: 30) TaqRRR-5 (SEQ ID NO: 32) rr5 (SEQ ID NO: 38) | TaqAYR-3 (SEQ ID NO: 31) TaqRRR-3 (SEQ ID NO: 33) rr3 (SEQ ID NO: 39) |

(2) Production and Purification of Variant Taq Polymerase

The production of variant Taq polymerases was carried out in the following manner. Using variant plasmid prepared in Example 1(2), E. coli BL21-CodonPlus-RIL strain (manufactured by Agilent Biotechnologies) was transformed according to the instruction manual.

At a point where OD600 of this culture broth reached 0.2 to 0.3, IPTG (manufactured by Wako Pure Chemical Industries, Ltd.) was added thereto so as to have a final concentration of 1 mM. The mixture was subjected to shaking culture at 25° C. for 14 hours for inducing expression of genes of intended proteins, and the culture broth was centrifuged (5,000×g, 10 minutes) to harvest bacterial cells. The obtained bacterial cells were washed with a PBS solution (150 mM NaCl, 20 mM $Na_2HPO_4$, and 2 mM $NaH_2PO_4$, pH 7.5). The bacterial cells were suspended in Solution A [50 mM Tris-HCl, pH 8.0, 1 mM EDTA, and 1 mM phenylmethylsulfonyl fluoride (PMSF) (manufactured by Wako Pure Chemical Industries, Ltd.)], and the bacterial cells were disrupted by sonication on ice. The disruption was centrifuged (23,700×g, 4° C., 10 minutes), and the supernatant thereof was heat-treated at 80° C. for 20 minutes and centrifuged (23,700×g, 4° C., 10 minutes). Sodium chloride was added to the obtained supernatant so as to have a final concentration of 1 M, 5% solution of polyethyleneimine (manufactured by Sigma-Aldrich) was added to the solution so as to have final concentration of 0.15% (w/v), and thereafter the mixture was allowed to stand for 30 minutes on ice. Ammonium sulfate was added to the supernatant obtained by centrifugation (23,700×g, 4° C., 10 minutes) so as to provide a 80% saturated solution. After centrifugation (23,700×g, 4° C., 10 minutes), precipitates were dissolved in Solution B [50 mM Tris-HCl, pH 8.0, and 1 M $(NH_4)_2SO_4$], the solution was applied to a hydrophobic column HiTrap Butyl FF 5 ml (manufactured by GE Healthcare) equilibrated with Solution B, and proteins were eluted by concentration gradients of ammonium sulfate of from 1 M to 0 M. The eluted fractions were dialyzed with Solution C [50 mM Tris-HCl, pH 8.0, and 50 mM NaCl] using a cellulose tube for dialysis, the solution was applied to an affinity column HiTrap Heparin HP 1 ml (manufactured by GE Healthcare) equilibrated with Solution C, and proteins were eluted by concentration gradients of sodium chloride of from 50 mM to 1 M. The eluted fraction was dialyzed with Solution C, the solution was finally applied to an anion exchange column HiTrap Q HP 1 ml (manufactured by GE Healthcare), and proteins were eluted by concentration gradients of sodium chloride of from 50 mM to 0.5 M. The obtained proteins were subjected to 12% SDS-PAGE, and CBB staining was carried out in accordance with a conventional method to examine the purity. Taq5 to Taq59 and Taq62 to 65 were subjected to protein production and purification according to the above methods. The results were shown in FIG. 1.

As shown in FIG. 1, it was confirmed that the produced proteins showed a single band, and that the proteins were purified. In addition, the amino acid sequences of the variants Taq55 to 59 and 62 to 65 obtained were shown in SEQ ID NOs: 40 to 48 of the Sequence Listing.

(3) Primer Extension Activity

For the measurement of primer extension activity of wild-type and variant TaqLF, primed-DNA in which 55 nt of oligonucleotide (M13-pri55, SEQ ID NO: 49) radioactive-labeled with [$\gamma$-$^{32}$P]ATP at 5' terminal was annealed to 2,961 nt of a cyclic single-stranded DNA [pBlueScript II SK(+) (manufactured by Agilent Biotechnologies)] was used as a substrate DNA.

A wild-type TaqLF or variant TaqLF was mixed in 20 µl of Liquid Reaction Mixture D [20 mM Tris-HCl, pH 8.8, 10 mM KCl, 3.5 mM MgCl$_2$, 0.1 mg/ml BSA, 0.1% Tween20, 5 nM primed-DNA and 0.25 mM dNTP] so as to have concentration of 10 nM, and the mixture was reacted at 72° C. for 2.5 minutes or 10 minutes. Two microliters of a reaction stop solution [300 mM NaOH, 6 mM EDTA, 18% Ficoll 400, 0.15% bromocresol green and 0.24% xylene cyanol] was added to 8 µl of each reaction mixture to stop the reaction. This reaction mixture was applied to 0.8% alkaline agarose gel, and electrophoresed in an alkaline solution [50 mM NaOH and 1 mM EDTA]. After electrophoresis, the gel was dried, and the dried gel was exposed to imaging plate (manufactured by FUJIFILM). The synthesized DNA was detected using Typhoon TRIO+ (GE Healthcare). The results of the primer extension activities of wild-type and each variant Taq polymerases are shown in FIG. 2-1 and FIG. 2-2.

As shown in FIG. 2-1, TaqLF WT was already 3.2 kb corresponding to one round of the template at a reaction for 2.5 minutes, and a strong band at 3.8 kb and a weak band at a position of 6 kb were detected at a reaction for 10 minutes.

On the other hand, Taq55 was extended to 3.4 kb at a reaction for 2.5 minutes. At 10 minutes, a strong band up to a position of 4.3 kb and a weak band up to a position of 7 kb were found.

Taq56 was extended to 4.3 kb at a reaction for 2.5 minutes. At 10 minutes, a strong band up to a position of 6.5 kb and a weak band up to a position of 9 kb were found.

Taq57 was extended to 6.5 kb at a reaction for 2.5 minutes. At 10 minutes, a strong band up to a position of 10 kb or more was found.

Taq58 was extended to 7.0 kb at a reaction for 2.5 minutes. At 10 minutes, a strong band up to a position of 10 kb or more was found.

Taq59 was extended to 8.0 kb at a reaction for 2.5 minutes. At 10 minutes, a strong band up to a position of 10 kb or more was found.

The sequence of the template DNA binding site of TaqLF WT is PYE, and the charge thereof is −1. The charge of Taq55 is 0, the charge of Taq56 is +1, the charges of Taq57 and Taq58 are +2, and the charge of Taq59 is +3. It could be seen from this matter that extension activity becomes larger, and also SD activity increases as the charge becomes positive.

Further, for the increase of extension activity, Taq59 and Taq62 to Taq65 were studied. An evaluation method is the same as the method mentioned above. Concretely, as shown in FIG. 2-2, for Taq62 to Taq65 in which amino acids at E742 site or E742 and A743 sites of variant Taq59 were mutated with those with a positive charge, improvement in the strand displacement activity was found more than that of Taq59. It could be confirmed from the above that the strand displacement activity can be improved by combining substitution of an amino acid sequence at 685 to 687 positions corresponding to a template DNA binding site of a Taq DNA polymerase and substitution of an amino acid sequence of other sites.

Example 2

Measurement of Binding Ability to Primed DNA According to Gel Shift Method

The affinity of variant Taq polymerases and primed DNAs was examined using a gel shift assay. The measurement was carried out in the following manner.

First, DNA in which a 27 nt of a single-stranded DNA (d27, SEQ ID NO: 50) radioactive-labeled with $^{32}$P at 5'-terminal was annealed to a non-labeled 49 nt of a single-stranded DNA (49N, SEQ ID NO: 51) was used as a substrate DNA for the measurement of DNA binding ability. DNA polymerase proteins were added to 10 µl of Solution E [20 mM Tris-HCl, pH 8.8, 10 mM NaCl, 5 mM MgCl$_2$, 14 mM 2-mercaptoethanol, 0.1 mg/ml BSA and 5% (v/v) glycerol] containing 2 nM substrate DNA so as to have concentration of from 0.6 to 400 nM, and the mixture was held at 40° C. for 5 minutes. A liquid DNA-enzyme mixture was subjected to 1% agarose gel and electrophoresed in a 0.1×TAE solution [4 mM Tris base, 2 mM acetic acid and 0.1 mM EDTA]. After the termination of electrophoresis, the gel was dried, and the dried gel was exposed to an imaging plate. Typhoon TRIO+ was used to detect a labeled DNA.

The results of gel shift assay were shown in FIG. 3.

From the previous results [*Front Microbiol.*, 5, 461, (2014), doi: 10.3389/fmicb.2014.00461], the apparent dissociation constant Kd value of wild-type Taq polymerase and the primed DNA was 400 nM.

On the other hand, for the Taq55 to Taq59 variants, in Taq57 and Taq58 with charges in the region of +2, Taq57 did not show a shifted band, but an amount of primed DNA was decreased by addition of 400 nM proteins. In Taq58, a shifted band was appeared at an amount of 25 nM proteins, and the apparent Kd value was 100 nM.

Next, in Taq59 with a charge of +3, the clear shifted band was appeared at 25 nM proteins, and a two-step shift was found at 400 nM. The apparent Kd value was 40 nM.

From the above results, there was a correlation between the primer extension activity and gel shift.

Example 3

Amplification of Genomic DNA Using Taq59 Polymerase (1) Comparison to Known Taq DNA Polymerases DNA amplification was carried out with Taq59 prepared in Example 1 using Pfu genomic DNA as a template. A composition of a liquid reaction mixture is 8 nM Taq59 polymerase, x1 SD buffer, 0.5 mM dNTPs, 10 ng Pfu genomic DNA, 10 µM pd(N)6, and 0.25 mg/ml of BSA. The reaction was carried out (A) at 50° C. for 6 hours, or (B) in 99 cycles of reactions, wherein one cycle is 30° C. for 60 seconds and 68° C. for 60 seconds. Also, a wild-type Taq DNA polymerase having the amino acid sequence shown in SEQ ID NO: 1 of the Sequence Listing, a Taq DNA polymerase Large Fragment having the amino acid sequence shown in SEQ ID NO: 3 of the Sequence Listing and a commercially available product SD-polymerase (manufactured by BIORON) having an SD activity were used as control samples.

The formed products were separated with 0.7% agarose gel, and stained with SYBR(registered trademark) Gold Nucleic Acid Gel Stain (manufactured by Thermo Fisher Scientific). The results were shown in FIG. 4.

As shown in FIGS. 4(A) and (B), amplified bands could not be obtained in the wild-type Taq DNA polymerase, the Taq DNA polymerase Large Fragment and the SD-polymerase under each of the conditions, but in the Taq59 of the present invention, bands could be obtained at boundary of the applied well and the gel.

Next, formed products were analyzed using an alkaline agarose gel.

First, the analysis was carried out at two patterns of extension temperatures of (A) 50° C. and (B) 70° C. The reaction was carried out in 20 μl of a liquid reaction mixture containing 32 nM polymerase, 20 mM Tris-HCl, pH 8.8, 10 mM KCl, 3.5 mM $MgCl_2$, 0.1% Tween20, 0.5 mM dNTPs, 10 ng Pfu genome DNA, 10 μM pd(N)6, and 0.25 mg/ml BSA in 60 cycles, wherein one cycle is 40° C. for 10 seconds, 50° C. for 1 minute, and 50° C. or 70° C. for 5 minutes. The products obtained were subjected to 0.8% alkaline agarose gel electrophoresis and stained with SYBR (registered trademark) Green II Nucleic Acid Gel Stain (manufactured by TAKARA BIO INC.). The results were shown in FIG. 5.

As shown in FIG. 5, wild-type Taq DNA polymerase and Taq DNA polymerase Large Fragments hardly showed any DNA amplification at an extension temperature of 50° C., but Taq59 of the present invention was found to show an amplification of high-molecular DNA between 23.1 kb of marker and wells.

At an extension temperature of 70° C., a DNA was amplified in a wide range up to 23 kb in the wild-type Taq DNA polymerase. On the other hand, a DNA was not amplified in the Taq large fragment. Amplification of high-molecular DNA was found between 23.1 kb marker and wells in Taq59. As described above, it could be seen that the DNA polymerase of the present invention has high thermostability. Further, it could be seen that the DNA polymerase of the present invention can efficiently replicate even a DNA having a long-strand length of 23 kb or more.

Next, the DNA amplification was carried out in the concentration of Taq59 ranging from 1 to 32 nM.

A reaction composition is 20 mM Tris-HCl, pH 8.8, 10 mM KCl, 3.5 mM $MgCl_2$, 0.1% Tween20, 0.5 mM dNTPs, 10 ng Pfu genome DNA, 10 μM pd(N)6, and 0.25 mg/ml BSA. The reaction was carried out at 50° C. for 6 hours. The formed products ([0082]) were subjected to a 0.8% alkaline agarose gel electrophoresis, and stained with SYBR(registered trademark) Green II Nucleic Acid Gel Stain. The results were shown in FIG. 6.

As shown in FIG. 6, the density of the bands became concentrated proportionally to an enzyme concentration at a concentration of Taq59 from 1 to 8 nM, and the density of the bands stayed at a given level at a density equal to or more than the range mentioned above. The position of the bands was lower than the wells.

(2) Comparison to phi29 DNA Polymerase

Taq59 of the present invention was compared to a commercially available phi29 DNA polymerase. A phi29 DNA polymerase used in this experiment is manufactured by New England Biolabs (trade name: phi29 DNA Polymerase), and known to have a very strong strand displacement activity.

In the reaction, 20 μl of a liquid reaction mixture containing 50 mM Tris-HCl, pH 7.5, 10 mM $(NH_4)_2SO_4$, 10 mM $MgCl_2$, 4 mM DTT, 0.5 mM dNTPs, 10 ng Pfu genome DNA, 10 μM pd(N)6, and 0.25 mg/ml BSA was used. The above-mentioned commercially available polymerase was added to the liquid reaction mixture in an amount of 10 U, and the reaction was carried out at 30° C. for 18 hours. The formed products and the formed products of [0082] were subjected to a 0.8% alkaline agarose gel electrophoresis, and stained with SYBR(registered trademark) Green II Nucleic Acid Gel Stain. The results were shown in FIG. 6.

As shown in FIG. 6, a DNA was amplified between 23 kb marker and wells in the phi29 DNA polymerase. On the other hand, it could be confirmed that the amount of amplified products is large in Taq59 of the present invention, as compared to the phi29 DNA polymerase. It could be confirmed from this matter that the DNA polymerase of the present invention having a strand displacement activity is more suitable for genome amplification than the phi29 DNA polymerase. As described above, it could be seen that the DNA polymerase of the present invention has a strong strand displacement activity.

INDUSTRIAL APPLICABILITY

The DNA polymerase of the present invention having a strand displacement activity has high thermostability, is capable of efficiently replicating a long-strand of a template DNA, and has a strong strand displacement activity, thereby making it possible to efficiently replicate a long-strand of a template DNA. The DNA polymerase having a strand displacement activity is useful in the broad fields such as genetic engineering, biology, medicine, and agriculture.

SEQUENCE LISTING FREE TEXT

SEQ ID NO: 1: Amino acid sequence of Taq DNA polymerase wild type
SEQ ID NO: 2: Nucleotide sequence of Taq DNA polymerase wild type
SEQ ID NO: 3: Amino acid sequence of Taq DNA polymerase large fragment
SEQ ID NO: 4: Nucleotide sequence of Taq DNA polymerase large fragment
SEQ ID NO: 5: Nucleotide sequence of DNA polymerase variant Taq55
SEQ ID NO: 6: Nucleotide sequence of DNA polymerase variant Taq56
SEQ ID NO: 7: Nucleotide sequence of DNA polymerase variant Taq57
SEQ ID NO: 8: Nucleotide sequence of DNA polymerase variant Taq58
SEQ ID NO: 9: Nucleotide sequence of DNA polymerase variant Taq59
SEQ ID NO: 10: Mutagenesis primer TaqPYA-5
SEQ ID NO: 11: Mutagenesis primer TaqPYA-3
SEQ ID NO: 12: Mutagenesis primer TaqPYK-5
SEQ ID NO: 13: Mutagenesis primer TaqPYK-3
SEQ ID NO: 14: Mutagenesis primer TaqPRK-5
SEQ ID NO: 15: Mutagenesis primer TaqPRK-3
SEQ ID NO: 16: Mutagenesis primer TaqSRK-5
SEQ ID NO: 17: Mutagenesis primer TaqSRK-3
SEQ ID NO: 18: Mutagenesis primer TaqRRR-5
SEQ ID NO: 19: Mutagenesis primer TaqRRR-3
SEQ ID NO: 20: Nucleotide sequence of DNA polymerase variant Taq62

SEQ ID NO: 21: Nucleotide sequence of DNA polymerase variant Taq63
SEQ ID NO: 22: Nucleotide sequence of DNA polymerase variant Taq64
SEQ ID NO: 23: Nucleotide sequence of DNA polymerase variant Taq65
SEQ ID NO: 24: Mutagenesis primer TaqAYR-5
SEQ ID NO: 25: Mutagenesis primer TaqAYR-3
SEQ ID NO: 26: Mutagenesis primer TaqRRR-5
SEQ ID NO: 27: Mutagenesis primer TaqRRR-3
SEQ ID NO: 28: Mutagenesis primer aa5
SEQ ID NO: 29: Mutagenesis primer aa3
SEQ ID NO: 30: Mutagenesis primer TaqAYR-5
SEQ ID NO: 31: Mutagenesis primer TaqAYR-3
SEQ ID NO: 32: Mutagenesis primer TaqRRR-5
SEQ ID NO: 33: Mutagenesis primer TaqRRR-3
SEQ ID NO: 34: Mutagenesis primer ha5
SEQ ID NO: 35: Mutagenesis primer ha3
SEQ ID NO: 36: Mutagenesis primer hk5
SEQ ID NO: 37: Mutagenesis primer hk3
SEQ ID NO: 38: Mutagenesis primer rr5
SEQ ID NO: 39: Mutagenesis primer rr3
SEQ ID NO: 40: Amino acid sequence of DNA polymerase variant Taq55
SEQ ID NO: 41: Amino acid sequence of DNA polymerase variant Taq56
SEQ ID NO: 42: Amino acid sequence of DNA polymerase variant Taq57
SEQ ID NO: 43: Amino acid sequence of DNA polymerase variant Taq58
SEQ ID NO: 44: Amino acid sequence of DNA polymerase variant Taq59
SEQ ID NO: 45: Amino acid sequence of DNA polymerase variant Taq62
SEQ ID NO: 46: Amino acid sequence of DNA polymerase variant Taq63
SEQ ID NO: 47: Amino acid sequence of DNA polymerase variant Taq64
SEQ ID NO: 48: Amino acid sequence of DNA polymerase variant Taq65
SEQ ID NO: 49: 55 nt Oligonucleotides M13-pri55
SEQ ID NO: 50: 27 nt Oligonucleotides d27
SEQ ID NO: 51: 49 nt Oligonucleotides 49N
SEQ ID NO: 52: Amino acid sequence of Pyrococcus furiosus RFC-L PIP-box

The invention claimed is:

1. A recombinant DNA polymerase having one or more amino acid substitutions to increase a total charge at a template DNA binding site, wherein the DNA polymerase is of *Thermus aquaticus*, *Thermus thermophilus*, or *Thermus flavus*, wherein the recombinant DNA polymerase does not have a 5'→3' exonuclease activity, wherein the recombinant DNA polymerase has a strand displacement activity, and wherein a template DNA binding site corresponds to amino acid positions 685 to 687 of the sequence as set forth in SEQ ID NO:1, and wherein the recombinant DNA polymerase has a sequence identity of 95% or more to the amino acid sequence of SEQ ID NO: 1.

2. The recombinant DNA polymerase according to claim 1, wherein the amino acid substitution is at an amino acid residue of the template DNA binding site, wherein the amino acid residue of the template DNA binding site is substituted with arginine, lysine, histidine, serine or alanine.

3. The recombinant DNA polymerase according to claim 1, having one or more substitutions selected from the group consisting of:
   (1) a substitution of from an amino acid corresponding to 685th proline to arginine or serine,
   (2) a substitution of from an amino acid corresponding to 686th tyrosine to arginine, and
   (3) a substitution of from an amino acid corresponding to 687th glutamic acid to arginine, lysine or alanine,
   of an amino acid sequence of the Taq DNA polymerase.

4. The recombinant DNA polymerase according to claim 1, wherein the DNA polymerase is a thermostable DNA polymerase.

5. The recombinant DNA polymerase according to claim 1, wherein the DNA polymerase is a Taq DNA polymerase having deletion of 289 amino acid residues from the N-terminus.

6. A nucleic acid comprising a nucleotide sequence encoding the DNA polymerase of claim 1.

7. A nucleic acid encoding the DNA polymerase of claim 1, comprising the nucleotide sequence as set forth in SEQ ID NO:5, 6, 7, 8, 9, 20, 21, 22, or 23.

8. A vector comprising the nucleic acid of claim 6.

9. A transformant comprising the vector of claim 8.

10. A method for producing a DNA polymerase, the method comprising culturing the transformant of claim 9, and harvesting the DNA polymerase from the cultured product.

11. A method for producing a DNA molecule, comprising incubating the DNA polymerase of claim 1 together with a template DNA.

12. The method according to claim 11, wherein the method is performed by a polymerase chain reaction or a reaction for isothermal nucleic acid amplification.

13. A kit comprising the DNA polymerase of claim 1.

14. A transformant comprising the nucleic acid of claim 6.

15. A transformant comprising the nucleic acid of claim 7.

16. The recombinant DNA polymerase according to claim 1, wherein the recombinant DNA polymerase further has a deletion of an N-terminal region compared to a wild-type of the DNA polymerase having sequence identity of 95% or more to the amino acid sequence of SEQ ID NO:1.

17. A DNA polymerase having a sequence identity of 95% or more to the amino acid sequence of SEQ ID NO:1 excluding the N-terminal amino acids 1-289, wherein the polymerase further has one or more amino acid substitutions at a DNA binding site corresponding to positions 685 to 687 to increase a total charge at the template DNA binding site, and wherein the DNA polymerase does not have a 5'→3' exonuclease activity.

18. The DNA polymerase of claim 17, wherein the one or more substitutions are selected from the group consisting of arginine or serine at the residue corresponding to position 685 of SEQ ID NO:1; arginine at the residue corresponding to position 686 of SEQ ID NO:1; and arginine, lysine or alanine at the residue corresponding to position 687 of SEQ ID NO:1.

19. A DNA polymerase comprising the amino acid sequence as set forth in SEQ ID NO:40, 41, 42, 43, 44, 45, 46, 47, or 48.

* * * * *

SEQUENCE LISTING

```
<160> NUMBER OF SEQ ID NOS: 52

<210> SEQ ID NO 1
<211> LENGTH: 832
<212> TYPE: PRT
<213> ORGANISM: Thermus aquaticus

<400> SEQUENCE: 1

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205
```

-continued

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr

```
                625                 630                 635                 640
Glu Thr Ala Ser Trp Met Phe Gly Val Pro Arg Glu Ala Val Asp Pro
                    645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
        690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                    725                 730                 735
Val Lys Ser Val Arg Glu Ala Ala Glu Arg Met Ala Phe Asn Met Pro
                740                 745                 750
Val Gln Gly Thr Ala Ala Asp Leu Met Lys Leu Ala Met Val Lys Leu
            755                 760                 765
Phe Pro Arg Leu Glu Glu Met Gly Ala Arg Met Leu Leu Gln Val His
        770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                    805                 810                 815
Leu Glu Val Glu Val Gly Ile Gly Glu Asp Trp Leu Ser Ala Lys Glu
                820                 825                 830

<210> SEQ ID NO 2
<211> LENGTH: 2499
<212> TYPE: DNA
<213> ORGANISM: Thermus aquaticus

<400> SEQUENCE: 2 atgagggggga tgctgcccct cttgagccc aagggccggg tcctcctggt ggacggccac    60
cacctggcct accgcacctt ccacgccctg aagggcctca ccaccagccg ggggagccg    120
gtgcaggcgg tctacggctt cgccaagagc ctcctcaagg ccctcaagga ggacggggac   180
gcggtgatcg tggtctttga cgccaaggcc cctccttcc gccacgaggc ctacggggg    240
tacaaggcgg ccgggccccc acgccggag gactttcccc ggcaactcgc cctcatcaag   300
gagctggtgg acctcctggg gctggcgcgc tcgaggtcc gggctacga gcggacgac    360
gtcctggcca gctggccaa gaaggcggaa aaggagggct acgaggtccg catcctcacc   420
gccgacaaag acctttacca gctcctttcc gaccgcatcc acgtcctcca ccccgagggg   480
tacctcatca cccggcctg gctttgggaa agtacggcc tgaggcccga ccagtgggcc   540
gactaccggg ccctgaccgg ggacgagtcc gacaacttc ccggggtcaa gggcatcggg   600
gagaagacgg cgaggaagct tctggaggag tgggggagcc tggaagccct cctcaagaac   660
ctggaccggc tgaagcccgc catccgggag aagatcctgg cccacatgga cgatctgaag   720
ctctcctggg acctggccaa ggtgcgcacc gacctgcccc tggaggtgga cttcgccaaa   780
aggcgggagc ccgaccggga gaggcttagg gcctttctgg agaggcttga gtttggcagc   840
ctcctccacg agttcggcct tctggaaaag cccaaggccc tggaggaggc ccccctggccc   900
ccgccggaag ggccttcgt gggctttgtg ctttcccgca aggagcccat gtgggccgat   960
cttctggccc tggccgccgc caggggggc cgggtccacc gggcccccga gccttataaa   1020
```

```
gccctcaggg acctgaagga ggcgcggggg cttctcgcca aagacctgag cgttctggcc    1080
ctgagggaag gccttggcct cccgcccggc gacgacccca tgctcctcgc ctacctcctg    1140 gaccccttcca acaccacccc cgaggggg tg gcccggcgct acggcgggga gtggacggag    1200
gaggcggggg agcgggccgc cctttccgag aggctcttcg ccaacctgtg ggggaggctt    1260
gagggggagg agaggctcct ttggctttac cgggaggtgg agaggcccct ttccgctgtc    1320
ctggcccaca tggaggccac ggggg tgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgga aagaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct tcaaccagac ggccacggcc acgggcaggc taagtagctc cgatcccaac    1740
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggacccct gatgcgccgg    1980 gcggccaaga ccatcaactt cggggtcctc tacggcatgt cggcccaccg cctctcccag    2040
gagctagcca tcccttacga ggaggccag gccttcattg agcgctactt tcagagcttc    2100
cccaaggtgc gggcctggat tgagaagacc ctggaggagg caggaggcg ggggtacgtg    2160 gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggagggggtg tatccccctgg ccgtgcccct ggaggtggag    2460
gtggggatag ggaggactg gctctccgcc aaggagtga                            2499
```

<210> SEQ ID NO 3
<211> LENGTH: 544
<212> TYPE: PRT
<213> ORGANISM: Artificial Sequence
<220> FEATURE:
<223> OTHER INFORMATION: Amino acid sequence of Taq DNA polymerase large
      fragment

<400> SEQUENCE: 3

```
Met Ser Pro Lys Ala Leu Glu Glu Ala Pro Trp Pro Pro Glu Gly
1               5                   10                  15

Ala Phe Val Gly Phe Val Leu Ser Arg Lys Glu Pro Met Trp Ala Asp
            20                  25                  30

Leu Leu Ala Leu Ala Ala Ala Arg Gly Gly Arg Val His Arg Ala Pro
        35                  40                  45

Glu Pro Tyr Lys Ala Leu Arg Asp Leu Lys Glu Ala Arg Gly Leu Leu
    50                  55                  60

Ala Lys Asp Leu Ser Val Leu Ala Leu Arg Glu Gly Leu Gly Leu Pro
65                  70                  75                  80

Pro Gly Asp Asp Pro Met Leu Leu Ala Tyr Leu Leu Asp Pro Ser Asn
                85                  90                  95
```

```
Thr Thr Pro Glu Gly Val Ala Arg Arg Tyr Gly Gly Glu Trp Thr Glu
            100                 105                 110

Glu Ala Gly Glu Arg Ala Ala Leu Ser Glu Arg Leu Phe Ala Asn Leu
        115                 120                 125

Trp Gly Arg Leu Glu Gly Glu Arg Leu Leu Trp Leu Tyr Arg Glu
130                 135                 140

Val Glu Arg Pro Leu Ser Ala Val Leu Ala His Met Glu Ala Thr Gly
145                 150                 155                 160

Val Arg Leu Asp Val Ala Tyr Leu Arg Ala Leu Ser Leu Glu Val Ala
                165                 170                 175

Glu Glu Ile Ala Arg Leu Glu Ala Glu Val Phe Arg Leu Ala Gly His
            180                 185                 190

Pro Phe Asn Leu Asn Ser Arg Asp Gln Leu Glu Arg Val Leu Phe Asp
        195                 200                 205

Glu Leu Gly Leu Pro Ala Ile Gly Lys Thr Glu Lys Thr Gly Lys Arg
    210                 215                 220

Ser Thr Ser Ala Ala Val Leu Glu Ala Leu Arg Glu Ala His Pro Ile
225                 230                 235                 240

Val Glu Lys Ile Leu Gln Tyr Arg Glu Leu Thr Lys Leu Lys Ser Thr
                245                 250                 255

Tyr Ile Asp Pro Leu Pro Asp Leu Ile His Pro Arg Thr Gly Arg Leu
            260                 265                 270

His Thr Arg Phe Asn Gln Thr Ala Thr Ala Thr Gly Arg Leu Ser Ser
        275                 280                 285

Ser Asp Pro Asn Leu Gln Asn Ile Pro Val Arg Thr Pro Leu Gly Gln
    290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Arg Asp Ile His Thr
            340                 345                 350

Glu Thr Ala Ser Trp Met Phe Gly Val Pro Arg Glu Ala Val Asp Pro
        355                 360                 365

Leu Met Arg Arg Ala Ala Lys Thr Ile Asn Phe Gly Val Leu Tyr Gly
    370                 375                 380

Met Ser Ala His Arg Leu Ser Gln Glu Leu Ala Ile Pro Tyr Glu Glu
385                 390                 395                 400

Ala Gln Ala Phe Ile Glu Arg Tyr Phe Gln Ser Phe Pro Lys Val Arg
                405                 410                 415

Ala Trp Ile Glu Lys Thr Leu Glu Glu Gly Arg Arg Gly Tyr Val
            420                 425                 430

Glu Thr Leu Phe Gly Arg Arg Arg Tyr Val Pro Asp Leu Glu Ala Arg
        435                 440                 445

Val Lys Ser Val Arg Glu Ala Ala Glu Arg Met Ala Phe Asn Met Pro
    450                 455                 460

Val Gln Gly Thr Ala Ala Asp Leu Met Lys Leu Ala Met Val Lys Leu
465                 470                 475                 480

Phe Pro Arg Leu Glu Glu Met Gly Ala Arg Met Leu Leu Gln Val His
                485                 490                 495

Asp Glu Leu Val Leu Glu Ala Pro Lys Glu Arg Ala Glu Ala Val Ala
            500                 505                 510
```

Arg Leu Ala Lys Glu Val Met Glu Gly Val Tyr Pro Leu Ala Val Pro
    515                 520                 525

Leu Glu Val Glu Val Gly Ile Gly Glu Asp Trp Leu Ser Ala Lys Glu
530                 535                 540

<210> SEQ ID NO 4
<211> LENGTH: 1635
<212> TYPE: DNA
<213> ORGANISM: Artificial Sequence
<220> FEATURE:
<223> OTHER INFORMATION: Nucleotide sequence of Taq DNA polymerase large
      fragment

<400> SEQUENCE: 4

| atgagcccca aggccctgga ggaggccccc tggcccccgc cggaaggggc cttcgtgggc | 60 |
| tttgtgcttt cccgcaagga gcccatgtgg gccgatcttc tggccctggc cgccgccagg | 120 |
| ggggccgggt ccaccgggc ccccgagcct tataaagccc tcagggacct gaaggaggcg | 180 |
| cggggcttc tcgccaaaga cctgagcgtt ctggccctga ggaaggcct tggcctcccg | 240 |
| cccggcgacg accccatgct cctcgcctac ctcctggacc cttccaacac cacccccgag | 300 |
| ggggtggccc ggcgctacgg cggggagtgg acggaggagg cggggagcg gccgcccctt | 360 |
| tccgagaggc tcttcgccaa cctgtggggg aggcttgagg gggaggagag gctcctttgg | 420 |
| cttttaccggg aggtggagag gccccttttcc gctgtcctgg cccacatgga ggccacgggg | 480 |
| gtgcgcctgg acgtggccta tctcaggcc ttgtccctgg aggtggccga ggagatcgcc | 540 |
| cgcctcgagg ccgaggtctt ccgcctggcc ggccacccct caacctcaa ctcccgggac | 600 |
| cagctggaaa gggtcctctt tgacgagcta gggcttcccg ccatcggcaa gacggagaag | 660 |
| accggcaagc gctccaccag cgccgccgtc ctggaggccc tccgcgaggc ccacccatc | 720 |
| gtggagaaga tcctgcagta ccgggagctc accaagctga gagcaccta cattgacccc | 780 |
| ttgccggacc tcatccaccc caggacgggc cgcctccaca cccgcttcaa ccagacggcc | 840 |
| acggccacgg gcaggctaag tagctccgat cccaacctcc agaacatccc cgtccgcacc | 900 |
| ccgcttgggc agaggatccg ccgggccttc atcgccgagg aggggtggct attggtggcc | 960 |
| ctggactata gccagataga gctcagggtg ctggcccacc tctccggcga cgagaacctg | 1020 |
| atccgggtct tccaggaggg gcgggacatc cacacggaga ccgccagctg gatgttcggc | 1080 |
| gtcccccggg aggccgtgga ccccctgatg cgccggcgg ccaagaccat caacttcggg | 1140 |
| gtcctctacg gcatgtcggc ccaccgcctc tcccaggagc tagccatccc ttacgaggag | 1200 |
| gcccaggcct tcattgagcg ctactttcag agcttcccca aggtgcgggc ctggattgag | 1260 |
| aagaccctgg aggagggcag gaggcggggg tacgtggaga ccctcttcgg ccgccgccgc | 1320 |
| tacgtgccag acctagaggc ccgggtgaag agcgtgcggg aggcggccga gcgcatggcc | 1380 |
| ttcaacatgc ccgtccaggg caccgccgcc gacctcatga agctggctat ggtgaagctc | 1440 |
| ttccccaggc tggaggaaat gggggccagg atgctcctc aggtccacga cgagctggtc | 1500 |
| ctcgaggccc caaaagagag gcggaggcc gtggcccggc tggccaagga ggtcatggag | 1560 |
| ggggtgtatc ccctggccgt gcccctggag gtggaggtgg ggataggga ggactggctc | 1620 |
| tccgccaagg agtga | 1635 |

<210> SEQ ID NO 5
<211> LENGTH: 1635
<212> TYPE: DNA
<213> ORGANISM: Artificial Sequence
<220> FEATURE:

<223> OTHER INFORMATION: Nucleotide sequence of DNA polymerase variant Taq55

<400> SEQUENCE: 5

```
atgagcccca aggccctgga ggaggccccc tggcccccgc cggaaggggc cttcgtgggc      60
tttgtgcttt cccgcaagga gcccatgtgg gccgatcttc tggccctggc cgccgccagg     120
ggggccgggt ccaccgggc ccccgagcct tataaagccc tcagggacct gaaggaggcg      180
cgggggcttc tcgccaaaga cctgagcgtt ctggccctga gggaaggcct tggcctcccg     240
cccggcgacg accccatgct cctcgcctac ctcctggacc cttccaacac cacccccgag     300
ggggtggccc ggcgctacgg cggggagtgg acggaggagg cggggagcg ggccgccctt      360
tccgagaggc tcttcgccaa cctgtggggg aggcttgagg gggaggagag gctccttttgg    420
ctttaccggg aggtggagag gcccctttcc gctgtcctgg cccacatgga ggccacgggg     480
gtgcgcctgg acgtggccta tctcagggcc ttgtccctgg aggtggccga ggagatcgcc     540
cgcctcgagg ccgaggtctt ccgcctggcc ggccaccccct tcaacctcaa ctcccgggac    600
cagctggaaa gggtcctctt tgacgagcta gggcttcccg ccatcggcaa gacggagaag     660
accggcaagc gctccaccag cgccgccgtc ctggaggccc tccgcgaggc ccaccccatc     720
gtggagaaga tcctgcagta ccgggagctc accaagctga gagcaccta cattgacccc      780
ttgccggacc tcatccaccc caggacgggc cgcctccaca cccgcttcaa ccagacggcc     840
acggccacgg gcaggctaag tagctccgat cccaacctcc agaacatccc cgtccgcacc     900
ccgcttgggc agaggatccg ccgggccttc atcgccgagg aggggtggct attggtggcc     960
ctggactata gccagataga gctcagggtg ctggcccacc tctccggcga cgagaacctg    1020
atccgggtct tccaggaggg gcgggacatc cacacggaga ccgccagctg gatgttcggc    1080
gtcccccggg aggccgtgga cccctgatg cgccgggcgg ccaagaccat caacttcggg     1140
gtcctctacg gcatgtcggc ccaccgcctc tcccaggagc tagccatccc ttacgcggag    1200
gcccaggcct tcattgagcg ctactttcag agcttcccca aggtgcgggc ctggattgag    1260
aagaccctgg aggagggcag gaggcggggg tacgtggaga ccctcttcgg ccgccgccgc    1320
tacgtgccag acctagaggc ccgggtgaag agcgtgcggg aggcggccga gcgcatggcc    1380
ttcaacatgc ccgtccaggg caccgccgcc gacctcatga agctggctat ggtgaagctc    1440
ttccccaggc tggaggaaat gggggccagg atgctccttc aggtccacga cgagctggtc    1500
ctcgaggccc caaaagagag ggcggaggcc gtggcccggc tggccaagga ggtcatggag    1560
ggggtgtatc ccctggccgt gcccctggag gtggaggtgg gataggggga ggactggctc    1620
tccgccaagg agtga                                                    1635
```

<210> SEQ ID NO 6
<211> LENGTH: 1635
<212> TYPE: DNA
<213> ORGANISM: Artificial Sequence
<220> FEATURE:
<223> OTHER INFORMATION: Nucleotide sequence of DNA polymerase variant Taq56

<400> SEQUENCE: 6

```
atgagcccca aggccctgga ggaggccccc tggcccccgc cggaaggggc cttcgtgggc      60
tttgtgcttt cccgcaagga gcccatgtgg gccgatcttc tggccctggc cgccgccagg     120
ggggccgggt ccaccgggc ccccgagcct tataaagccc tcagggacct gaaggaggcg      180
cgggggcttc tcgccaaaga cctgagcgtt ctggccctga gggaaggcct tggcctcccg     240
```

```
cccggcgacg accccatgct cctcgcctac ctcctggacc cttccaacac cacccccgag    300
ggggtggccc ggcgctacgg cggggagtgg acggaggagg cggggagcg ggccgccctt     360 tccgagaggc tcttcgccaa cctgtggggg aggcttgagg gggaggagag gctcctttgg    420
ctttaccggg aggtggagag gccccttttcc gctgtcctgg cccacatgga ggccacgggg   480
gtgcgcctgg acgtggccta tctcagggcc ttgtccctgg aggtggccga ggagatcgcc    540
cgcctcgagg ccgaggtctt ccgcctggcc ggccacccct tcaacctcaa ctcccgggac    600
cagctggaaa gggtcctctt tgacgagcta gggcttcccg ccatcggcaa gacggagaag    660
accggcaagc gctccaccag cgccgccgtc ctggaggccc tccgcgaggc ccaccccatc    720
gtggagaaga tcctgcagta ccgggagctc accaagctga gagcaccta cattgacccc    780 ttgccggacc tcatccaccc caggacgggc cgcctccaca cccgcttcaa ccagacggcc    840
acggccacgg gcaggctaag tagctccgat cccaacctcc agaacatccc cgtccgcacc    900
ccgcttgggc agaggatccg ccgggccttc atcgccgagg aggggtggct attggtggcc    960
ctggactata gccagataga gctcagggtg ctggcccacc tctccggcga cgagaacctg   1020
atccgggtct tccaggaggg gcgggacatc cacacgagaa ccgccagctg gatgttcggc   1080
gtcccccggg aggccgtgga cccctgatg cgccggcgg ccaagaccat caacttcggg     1140
gtcctctacg gcatgtcggc ccaccgcctc tcccaggagc tagccatccc ttacaaggag   1200
gcccaggcct tcattgagcg ctactttcag agcttcccca aggtgcgggc ctggattgag   1260
aagaccctgg aggagggcag gaggcggggg tacgtggaga ccctcttcgg ccgccgccgc   1320
tacgtgccag acctagaggc ccgggtgaag agcgtgcggg aggcggccga gcgcatggcc    1380
ttcaacatgc ccgtccaggg caccgccgcc gacctcatga agctggctat ggtgaagctc   1440
ttccccaggc tggaggaaat gggggccagg atgctccttc aggtccacga cgagctggtc   1500
ctcgaggccc caaaagagag ggcggaggcc gtgcccggc tggccaagga ggtcatggag    1560
ggggtgtatc ccctggccgt gccctgag gtggaggtgg gatagggga ggactggctc      1620 tccgccaagg agtga                                                    1635
```

<210> SEQ ID NO 7  
<211> LENGTH: 1635  
<212> TYPE: DNA  
<213> ORGANISM: Artificial Sequence  
<220> FEATURE:  
<223> OTHER INFORMATION: Nucleotide sequence of DNA polymerase variant Taq57

<400> SEQUENCE: 7

```
atgagcccca aggccctgga ggaggccccc tggcccccgc cggaaggggc cttcgtgggc     60
tttgtgcttt cccgcaagga gcccatgtgg gccgatcttc tggccctggc cgccgccagg    120 ggggccggg tccaccgggc ccccgagcct tataaagccc tcagggacct gaaggaggcg     180
cggggggctt cgccaaaga cctgagcgtt ctggccctga gggaaggcct tggcctcccg    240
cccggcgacg accccatgct cctcgcctac ctcctggacc cttccaacac cacccccgag    300
ggggtggccc ggcgctacgg cggggagtgg acggaggagg cggggagcg ggccgccctt     360 tccgagaggc tcttcgccaa cctgtggggg aggcttgagg gggaggagag gctcctttgg    420
ctttaccggg aggtggagag gccccttttcc gctgtcctgg cccacatgga ggccacgggg   480
gtgcgcctgg acgtggccta tctcagggcc ttgtccctgg aggtggccga ggagatcgcc    540
cgcctcgagg ccgaggtctt ccgcctggcc ggccacccct tcaacctcaa ctcccgggac    600
```

```
cagctggaaa gggtcctctt tgacgagcta gggcttcccg ccatcggcaa gacggagaag      660
accggcaagc gctccaccag cgccgccgtc ctggaggccc tccgcgaggc ccaccccatc      720
gtggagaaga tcctgcagta ccgggagctc accaagctga agagcaccta cattgacccc      780
ttgccggacc tcatccaccc caggacgggc cgcctccaca cccgcttcaa ccagacggcc      840
acggccacgg gcaggctaag tagctccgat cccaacctcc agaacatccc cgtccgcacc      900
ccgcttgggc agaggatccg ccgggccttc atcgccgagg aggggtggct attggtggcc      960
ctggactata gccagataga gctcagggtg ctggcccacc tctccggcga cgagaacctg     1020
atccgggtct ccaggagggc gcggacatc acacgcgaga ccgccagctg gatgttcggc      1080
gtcccccggg aggccgtgga ccccctgatg cgccgggcgg ccaagaccat caacttcggg     1140
gtcctctacg gcatgtcggc ccaccgcctc tcccaggagc tagccatccc tgcaaggag      1200 gcccaggcct tcattgagcg ctactttcag agcttcccca aggtgcgggc ctggattgag     1260
aagaccctgg aggagggcag gaggcggggg tacgtggaga ccctcttcgg ccgccgccgc     1320
tacgtgccag acctagaggc ccgggtgaag agcgtgcggg aggcggccga gcgcatggcc     1380
ttcaacatgc ccgtccaggg caccgccgcc gacctcatga agctggctat ggtgaagctc     1440
ttccccaggc tggaggaaat gggggccagg atgctccttc aggtccacga cgagctggtc     1500
ctcgaggccc caaaagagag ggcggaggcc gtgcccggc tggccaagga ggtcatggag      1560
ggggtgtatc ccctggccgt gcccctggag gtggaggtgg gataggggga ggactggctc     1620
tccgccaagg agtga                                                      1635
```

<210> SEQ ID NO 8
<211> LENGTH: 1635
<212> TYPE: DNA
<213> ORGANISM: Artificial Sequence
<220> FEATURE:
<223> OTHER INFORMATION: Nucleotide sequence of DNA polymerase variant
      Taq58

<400> SEQUENCE: 8

```
atgagcccca aggccctgga ggaggccccc tggcccccgc cggaagggc cttcgtgggc        60 tttgtgcttt cccgcaagga gcccatgtgg gccgatcttc tggccctggc cgccgccagg      120
ggggccgggg tccaccgggc ccccgagcct tataaagccc tcaggacct gaaggaggcg       180 cgggggcttc tcgccaaaga cctgagcgtt ctggccctga ggaaggcct tggcctcccg       240 cccggcgacg accccatgct cctcgcctac ctcctggacc cttccaacac caccccgag       300 ggggtggccc ggcgctacgg cggggagtgg acggaggagg cggggagcg gccgcccctt       360 tccgagaggc tcttcgccaa cctgtggggg aggcttgagg ggaggagag gctcctttgg      420 ctttaccggg aggtggagag gccccttttcc gctgtcctgg cccacatgga ggccacgggg   480
gtgcgcctgg acgtggccta tctcagggcc ttgtccctgg aggtggccga ggagatcgcc      540
cgcctcgagg ccgaggtctt ccgcctggcc ggccaccccct tcaacctcaa ctcccgggac     600
cagctggaaa gggtcctctt tgacgagcta gggcttcccg ccatcggcaa gacggagaag      660
accggcaagc gctccaccag cgccgccgtc ctggaggccc tccgcgaggc ccaccccatc      720
gtggagaaga tcctgcagta ccgggagctc accaagctga agagcaccta cattgacccc      780
ttgccggacc tcatccaccc caggacgggc cgcctccaca cccgcttcaa ccagacggcc      840
acggccacgg gcaggctaag tagctccgat cccaacctcc agaacatccc cgtccgcacc      900
ccgcttgggc agaggatccg ccgggccttc atcgccgagg aggggtggct attggtggcc      960
```

```
ctggactata gccagataga gctcaggrtg ctggcccacc tctccggcga cgagaacctg    1020
atccgggtct tccaggaggg gcgggacatc cacacgcaga ccgccagctg gatgttcggc    1080
gtcccccggg aggccgtgga ccccctgatg cgccgggcgg ccaagaccat caacttcggg    1140
gtcctctacg gcatgtcggc ccaccgcctc tcccaggagc tagccatctc tgcaaggag    1200 gcccaggcct tcattgagcg ctactttcag agcttcccca aggtgcgggc ctggattgag    1260
aagaccctgg aggagggcag gaggcggggg tacgtggaga ccctcttcgg ccgccgccgc    1320
tacgtgccag acctagaggc ccgggtgaag agcgtgcggg aggcggccga gcgcatggcc    1380
ttcaacatgc ccgtccaggg caccgccgcc gacctcatga agctggctat ggtgaagctc    1440
ttccccaggc tggaggaaat ggggggccagg atgctccttc aggtccacga cgagctggtc    1500
ctcgaggccc caaaagagag ggcggaggcc gtgcccggc tggccaagga ggtcatggag    1560
ggggtgtatc ccctggccgt gcccctggag gtggaggtgg gatagggga ggactggctc    1620 tccgccaagg agtga                                                    1635

<210> SEQ ID NO 9
<211> LENGTH: 1635
<212> TYPE: DNA
<213> ORGANISM: Artificial Sequence
<220> FEATURE:
<223> OTHER INFORMATION: Nucleotide sequence of DNA polymerase variant
      Taq59

<400> SEQUENCE: 9
atgagcccca aggccctgga ggaggccccc tggccccgc cggaaggggc cttcgtgggc      60
tttgtgcttt cccgcaagga gcccatgtgg gccgatcttc tggccctggc cgccgccagg    120
gggggccggg tccaccgggc ccccgagcct tataaagccc tcaggacct gaaggaggcg    180 cgggggcttc tcgccaaaga cctgagcgtt ctggccctga gggaaggcct tggcctcccg    240 cccgcgacg acccccatgct cctcgcctac tccctggacc cttccaacac cacccccgag    300
ggggtggccc ggcgctacgg cggggagtgg acggaggagg cgggggagcg ggccgccctt    360
tccgagaggc tcttcgccaa cctgtggggg aggcttgagg ggaggagag gctccttggg    420 ctttaccggg aggtggagag gcccctttcc gctgtcctgg cccacatgga ggccacgggg    480
gtgcgcctgg acgtggccta tctcagggcc ttgtccctgg aggtggccga ggagatcgcc    540
cgcctcgagg ccgaggtctt ccgcctggcc ggccaccccc tcaacctcaa ctcccgggac    600
cagctggaaa gggtcctctt tgacgagcta gggcttcccg ccatcggcaa gacgagaag    660 accggcaagc gctccaccag cgccgccgtc ctggaggccc tccgcgaggc ccaccccatc    720
gtggagaaga tcctgcagta ccgggagctc accaagctga agagcaccta cattgacccc    780
ttgccggacc tcatccaccc caggacgggc cgcctccaca cccgcttcaa ccagacggcc    840
acggccacgg gcaggctaag tagctccgat cccaacctcc agaacatccc cgtccgcacc    900
ccgcttgggc agaggatccg ccgggccttc atcgccgagg aggggtggct attggtggcc    960
ctggactata gccagataga gctcaggrtg ctggcccacc tctccggcga cgagaacctg    1020
atccgggtct tccaggaggg gcgggacatc cacacgcaga ccgccagctg gatgttcggc    1080
gtcccccggg aggccgtgga ccccctgatg cgccgggcgg ccaagaccat caacttcggg    1140
gtcctctacg gcatgtcggc ccaccgcctc tcccaggagc tagccatccg tcgccgtgag    1200
gcccaggcct tcattgagcg ctactttcag agcttcccca aggtgcgggc ctggattgag    1260
aagaccctgg aggagggcag gaggcggggg tacgtggaga ccctcttcgg ccgccgccgc    1320
```

```
tacgtgccag acctagaggc ccgggtgaag agcgtgcggg aggcggccga gcgcatggcc    1380
ttcaacatgc ccgtccaggg caccgccgcc gacctcatga agctggctat ggtgaagctc    1440
ttccccaggc tggaggaaat gggggccagg atgctccttc aggtccacga cgagctggtc    1500
ctcgaggccc caaaagagag ggcggaggcc gtggcccggc tggccaagga ggtcatggag    1560
ggggtgtatc ccctggccgt gccctggag gtggaggtgg ggatagggga ggactggctc     1620
tccgccaagg agtga                                                     1635
```

<210> SEQ ID NO 10
<211> LENGTH: 40
<212> TYPE: DNA
<213> ORGANISM: Artificial Sequence
<220> FEATURE:
<223> OTHER INFORMATION: Mutagenesis primer TaqPYA-5

<400> SEQUENCE: 10

```
ccaggagcta gccatccctt acgcggaggc ccaggccttc                            40
```

<210> SEQ ID NO 11
<211> LENGTH: 40
<212> TYPE: DNA
<213> ORGANISM: Artificial Sequence
<220> FEATURE:
<223> OTHER INFORMATION: Mutagenesis primer TaqPYA-3

<400> SEQUENCE: 11

```
gaaggcctgg gcctccgcgt aagggatggc tagctcctgg                            40
```

<210> SEQ ID NO 12
<211> LENGTH: 40
<212> TYPE: DNA
<213> ORGANISM: Artificial Sequence
<220> FEATURE:
<223> OTHER INFORMATION: Mutagenesis primer TaqPYK-5

<400> SEQUENCE: 12

```
ccaggagcta gccatccctt acaaggaggc ccaggccttc                            40
```

<210> SEQ ID NO 13
<211> LENGTH: 40
<212> TYPE: DNA
<213> ORGANISM: Artificial Sequence
<220> FEATURE:
<223> OTHER INFORMATION: Mutagenesis primer TaqPYK-3

<400> SEQUENCE: 13

```
gaaggcctgg gcctccttgt aagggatggc tagctcctgg                            40
```

<210> SEQ ID NO 14
<211> LENGTH: 40
<212> TYPE: DNA
<213> ORGANISM: Artificial Sequence
<220> FEATURE:
<223> OTHER INFORMATION: Mutagenesis primer TaqPRK-5

<400> SEQUENCE: 14

```
ccaggagcta gccatccctc gcaaggaggc ccaggccttc                            40
```

<210> SEQ ID NO 15
<211> LENGTH: 40
<212> TYPE: DNA
<213> ORGANISM: Artificial Sequence
<220> FEATURE:

```
<223> OTHER INFORMATION: Mutagenesis primer TaqPRK-3

<400> SEQUENCE: 15
gaaggcctgg gcctccttgc gagggatggc tagctcctgg                    40

<210> SEQ ID NO 16
<211> LENGTH: 40
<212> TYPE: DNA
<213> ORGANISM: Artificial Sequence
<220> FEATURE:
<223> OTHER INFORMATION: Mutagenesis primer TaqSRK-5

<400> SEQUENCE: 16
ccaggagcta gccatctctc gcaaggaggc ccaggccttc                    40

<210> SEQ ID NO 17
<211> LENGTH: 40
<212> TYPE: DNA
<213> ORGANISM: Artificial Sequence
<220> FEATURE:
<223> OTHER INFORMATION: Mutagenesis primer TaqSRK-3

<400> SEQUENCE: 17
gaaggcctgg gcctccttgc gagagatggc tagctcctgg                    40

<210> SEQ ID NO 18
<211> LENGTH: 45
<212> TYPE: DNA
<213> ORGANISM: Artificial Sequence
<220> FEATURE:
<223> OTHER INFORMATION: Mutagenesis primer TaqRRR-5

<400> SEQUENCE: 18
cccaggagct agccatccgt cgccgtgagg cccaggcctt cattg              45

<210> SEQ ID NO 19
<211> LENGTH: 45
<212> TYPE: DNA
<213> ORGANISM: Artificial Sequence
<220> FEATURE:
<223> OTHER INFORMATION: Mutagenesis primer TaqRRR-3

<400> SEQUENCE: 19
caatgaaggc ctgggcctca cggcgacgga tggctagctc ctggg              45

<210> SEQ ID NO 20
<211> LENGTH: 1635
<212> TYPE: DNA
<213> ORGANISM: Artificial Sequence
<220> FEATURE:
<223> OTHER INFORMATION: Nucleotide sequence of DNA polymerase variant
      Taq62

<400> SEQUENCE: 20
atgagcccca aggccctgga ggaggccccc tggcccccgc cggaagggc cttcgtgggc      60 tttgtgcttt cccgcaagga gcccatgtgg gccgatcttc tggccctggc cgccgccagg    120
gggggccggg tccaccgggc ccccgagcct tataaagccc tcagggacct gaaggaggcg    180
cgggggcttc tcgccaaaga cctgagcgtt ctggccctga ggaaggcct tggcctcccg    240 cccggcgacg accccatgct cctcgcctac ctcctggacc cttccaacac cacccccgag    300
ggggtggccc ggcgctacgg cggggagtgg acggaggagc gggggagcg ggccgcccttt   360 tccgagaggc tcttcgccaa cctgtggggg aggcttgagg gggaggagag gctcctttgg    420
```

```
ctttaccggg aggtggagag gccccttttcc gctgtcctgg cccacatgga ggccacgggg      480
gtgcgcctgg acgtggccta tctcagggcc ttgtccctgg aggtggccga ggagatcgcc      540
cgcctcgagg ccgaggtctt ccgcctggcc ggccacccct caacctcaa ctcccgggac       600 cagctggaaa gggtcctctt tgacgagcta gggcttcccg ccatcggcaa gacgagaaag     660
accggcaagc gctccaccag cgccgccgtc ctggaggccc tccgcgaggc cacccccatc     720
gtggagaaga tcctgcagta ccgggagctc accaagctga agagcaccta cattgacccc    780
ttgccggacc tcatccaccc caggacgggc cgcctccaca cccgcttcaa ccagacggcc    840
acggccacgg gcaggctaag tagctccgat cccaacctcc agaacatccc cgtccgcacc   900
ccgcttgggc agaggatccg ccgggccttc atcgccgagg aggggtggct attggtggcc   960
ctggactata gccagataga gctcagggtg ctggcccacc tctccggcga cgagaacctg  1020
atccgggtct tccaggaggg gcgggacatc cacacgagga ccgccagctg gatgttcggc  1080
gtcccccggg aggccgtgga ccccctgatg cgccgggcgg ccaagaccat caacttcggg  1140
gtcctctacg gcatgtcggc ctaccgcctc tcccaggagc tagccatccg tcgccgtgag  1200
gcccaggcct tcattgagcg ctactttcag agcttcccca aggtgcgggc ctggattgag  1260
aagaccctgg aggagggcag gaggcggggg tacgtggaga ccctcttcgg ccgccgccgc  1320
tacgtgccag acctagaggc ccgggtgaag agcgtgcggg cggcggccga gcgcatggcc  1380
ttcaacatgc ccgtccaggg caccgccgcc gacctcatga gctggctat ggtgaagctc   1440 ttccccaggc tggaggaaat gggggccagg atgctccttc aggtccacga cgagctggtc  1500
ctcgaggccc caaaagagag ggcggaggcc gtggcccggc tggccaagga ggtcatggag  1560
ggggtgtatc ccctggccgt gcccctggag gtggaggtgg ggatagggga ggactggctc  1620
tccgccaagg agtga                                                     1635
```

<210> SEQ ID NO 21
<211> LENGTH: 1635
<212> TYPE: DNA
<213> ORGANISM: Artificial Sequence
<220> FEATURE:
<223> OTHER INFORMATION: Nucleotide sequence of DNA polymerase variant Taq63

<400> SEQUENCE: 21

```
atgagcccca aggccctgga ggaggccccc tggccccgc cggaaggggc cttcgtgggc       60
tttgtgcttt cccgcaagga gcccatgtgg gccgatcttc tggccctggc cgccgccagg     120
gggggccggg tccaccgggc ccccgagcct tataaagccc tcagggacct gaaggaggcg     180
cgggggcttc tcgccaaaga cctgagcgtt ctggccctga gggaaggcct tggcctcccg    240 cccgcgacg accccatgct cctcgcctac tcctggacc cttccaacac cacccccgag      300
ggggtggccc ggcgctacgg cggggagtgg acggaggagg cggggagcg ggccgccctt    360 tccgagaggc tcttcgccaa cctgtggggg aggcttgagg ggaggagag gctcctttgg    420 ctttaccggg aggtggagag gccccttttcc gctgtcctgg cccacatgga ggccacgggg  480
gtgcgcctgg acgtggccta tctcagggcc ttgtccctgg aggtggccga ggagatcgcc   540
cgcctcgagg ccgaggtctt ccgcctggcc ggccacccct caacctcaa ctcccgggac    600 cagctggaaa gggtcctctt tgacgagcta gggcttcccg ccatcggcaa gacgagaaag   660
accggcaagc gctccaccag cgccgccgtc ctggaggccc tccgcgaggc cacccccatc   720
gtggagaaga tcctgcagta ccgggagctc accaagctga agagcaccta cattgacccc   780
```

| | |
|---|---|
| ttgccggacc tcatccaccc caggacgggc cgcctccaca cccgcttcaa ccagacggcc | 840 |
| acggccacgg gcaggctaag tagctccgat cccaacctcc agaacatccc cgtccgcacc | 900 |
| ccgcttgggc agaggatccg ccgggccttc atcgccgagg aggggtggct attggtggcc | 960 |
| ctggactata gccagataga gctcaggGtg ctggcccacc tctccggcga cgagaacctg | 1020 |
| atccgggtct tccaggaggg gcgggacatc cacacggaga ccgccagctg gatgttcggc | 1080 |
| gtcccccggg aggccgtgga ccccctgatg cgccgggcgg ccaagaccat caacttcggg | 1140 |
| gtcctctacg gcatgtcggc ctaccgcctc tcccaggagc tagccatccg tcgccgtgag | 1200 |
| gcccaggcct tcattgagcg ctactttcag agcttcccca aggtgcgggc ctggattgag | 1260 |
| aagaccctgg aggagggcag gaggcggggg tacgtggaga ccctcttcgg ccgccgccgc | 1320 |
| tacgtgccag acctagaggc ccgggtgaag agcgtcgcgc atgcggccga gcgcatggcc | 1380 |
| ttcaacatgc ccgtccaggg caccgccgcc gacctcatga gctggctat ggtgaagctc | 1440 |
| ttccccaggc tggaggaaat gggggccagg atgctccttc aggtccacga cgagctggtc | 1500 |
| ctcgaggccc caaaagagag ggcggaggcc gtggcccggc tggccaagga ggtcatggag | 1560 |
| ggggtgtatc ccctggccgt gccccctggag gtggaggtgg gataggggga ggactggctc | 1620 |
| tccgccaagg agtga | 1635 |

<210> SEQ ID NO 22
<211> LENGTH: 1635
<212> TYPE: DNA
<213> ORGANISM: Artificial Sequence
<220> FEATURE:
<223> OTHER INFORMATION: Nucleotide sequence of DNA polymerase variant Taq64

<400> SEQUENCE: 22

| | |
|---|---|
| atgagcccca aggccctgga ggaggccccc tggccccgc cggaaggggc cttcgtgggc | 60 |
| tttgtgcttt cccgcaagga gcccatgtgg ccgatcttc tggccctggc cgccgccagg | 120 |
| ggggccgggt ccaccgggc ccccgagcct tataaagccc tcagggacct gaaggaggcg | 180 |
| cgggggcttc tcgccaaaga cctgagcgtt ctggccctga gggaaggcct tggcctcccg | 240 |
| cccgcgacg acccccatgct cctcgcctac ctcctggacc cttccaacac cacccccgag | 300 |
| ggggtggccc ggcgctacgg cggggagtgg acggaggagg cgggggagcg ggccgccctt | 360 |
| tccgagaggc tcttcgccaa cctgtggggg aggcttgagg ggaggagag gctccttt gg | 420 |
| cttta ccggg aggtggagag gcccctttcc gctgtcctgg cccacatgga ggccacgggg | 480 |
| gtgcgcctga cgtggccta tctcaggggcc ttgtccctgg aggtggccga ggagatcgcc | 540 |
| cgcctcgagg ccgaggtctt ccgcctggcc ggccacccct tcaacctcaa ctcccgggac | 600 |
| cagctggaaa gggtcctctt tgacgagcta gggcttcccg ccatcggcaa gacggagaag | 660 |
| accggcaagc gctccaccag cgccgccgtc ctggaggccc tccgcgaggc ccaccccatc | 720 |
| gtggagaaga tcctgcagta ccgggagctc accaagctga agagcaccta cattgacccc | 780 |
| ttgccggacc tcatccaccc caggacgggc cgcctccaca cccgcttcaa ccagacggcc | 840 |
| acggccacgg gcaggctaag tagctccgat cccaacctcc agaacatccc cgtccgcacc | 900 |
| ccgcttgggc agaggatccg ccgggccttc atcgccgagg aggggtggct attggtggcc | 960 |
| ctggactata gccagataga gctcaggGtg ctggcccacc tctccggcga cgagaacctg | 1020 |
| atccgggtct tccaggaggg gcgggacatc cacacggaga ccgccagctg gatgttcggc | 1080 |
| gtcccccggg aggccgtgga ccccctgatg cgccgggcgg ccaagaccat caacttcggg | 1140 |

```
gtcctctacg gcatgtcggc ctaccgcctc tcccaggagc tagccatccg tcgccgtgag    1200
gcccaggcct tcattgagcg ctactttcag agcttcccca aggtgcgggc ctggattgag    1260
aagaccctgg aggagggcag gaggcggggg tacgtggaga ccctcttcgg ccgccgccgc    1320
tacgtgccag acctagaggc ccgggtgaag agcgtgcggc ataaagccga gcgcatggcc    1380
ttcaacatgc ccgtccaggg caccgccgcc gacctcatga agctggctat ggtgaagctc    1440
ttccccaggc tggaggaaat gggggccagg atgctccttc aggtccacga cgagctggtc    1500
ctcgaggccc caaaagagag gcggaggcc gtggcccggc tggccaagga ggtcatggag    1560
ggggtgtatc ccctggccgt gcccctggag gtggaggtgg gataggggga ggactggctc    1620
tccgccaagg agtga                                                    1635

<210> SEQ ID NO 23
<211> LENGTH: 1635
<212> TYPE: DNA
<213> ORGANISM: Artificial Sequence
<220> FEATURE:
<223> OTHER INFORMATION: Nucleotide sequence of DNA polymerase variant
      Taq65

<400> SEQUENCE: 23
atgagcccca aggccctgga ggaggccccc tggccccgc cggaaggggc cttcgtgggc      60
tttgtgcttt cccgcaagga gcccatgtgg gccgatcttc tggccctggc cgccgccagg    120
gggggccggg tccaccgggc ccccgagcct tataaagccc tcaggacct gaaggaggcg     180 cgggggcttc tcgccaaaga cctgagcgtt ctggccctga ggaaggcct tggcctcccg    240 cccggcgacg acccccatgct cctcgcctac ctcctggacc cttccaacac cacccccgag   300
ggggtggccc ggcgctacgg cggggagtgg acggaggagg cggggagcg ggccgccctt     360 tccgagaggc tcttcgccaa cctgtggggg aggcttgagg ggaggagag gctcctttgg    420 ctttaccggg aggtggagag gccccttttcc gctgtcctgg cccacatgga ggccacgggg   480
gtgcgcctgg acgtggccta tctcagggcc ttgtccctgg aggtggccga ggagatcgcc    540
cgcctcgagg ccgaggtctt ccgcctggcc ggccaccccct tcaacctcaa ctcccgggac   600
cagctggaaa gggtcctctt tgacgagcta gggcttcccg ccatcggcaa gacggagaag    660
accggcaagc gctccaccag cgccgccgtc ctggaggccc tccgcgaggc ccacccatc     720 gtggagaaga tcctgcagta ccgggagctc accaagctga gagcaccta cattgacccc    780 ttgccggacc tcatccaccc caggacgggc gcctccaca cccgcttcaa ccagacggcc    840
acggccacgg caggctaag tagctccgat cccaaccctcc agaacatccc cgtccgcacc    900
ccgcttgggc agaggatccg ccgggccttc atcgccgagg aggggtggct attggtggcc   960
ctggactata gccagataga gctcagggtg ctggcccacc tctccggcga cgagaacctg    1020
atccgggtct ccaggaggg gcgggacatc cacacgagga ccgccagctg gatgttcggc    1080
gtcccccggg aggccgtgga ccccctgatg cgccgggcgg ccaagaccat caacttcggg   1140
gtcctctacg gcatgtcggc ctaccgcctc tcccaggagc tagccatccg tcgccgtgag    1200
gcccaggcct tcattgagcg ctactttcag agcttcccca aggtgcgggc ctggattgag    1260
aagaccctgg aggagggcag gaggcggggg tacgtggaga ccctcttcgg ccgccgccgc    1320
tacgtgccag acctagaggc ccgggtgaag agcgtgcggc gccgcccga gcgcatggcc    1380 ttcaacatgc ccgtccaggg caccgccgcc gacctcatga agctggctat ggtgaagctc    1440
ttccccaggc tggaggaaat gggggccagg atgctccttc aggtccacga cgagctggtc    1500
```

```
ctcgaggccc caaaagagag ggcggaggcc gtggcccggc tggccaagga ggtcatggag    1560
ggggtgtatc ccctggccgt gccoctggag gtggaggtgg ggataggga ggactggctc     1620 tccgccaagg agtga                                                      1635
```

```
<210> SEQ ID NO 24
<211> LENGTH: 42
<212> TYPE: DNA
<213> ORGANISM: Artificial Sequence
<220> FEATURE:
<223> OTHER INFORMATION: Mutagenesis primer TaqAYR-5

<400> SEQUENCE: 24
cctctacggc atgtcggcct accgcctctc ccaggagcta gc                        42

<210> SEQ ID NO 25
<211> LENGTH: 42
<212> TYPE: DNA
<213> ORGANISM: Artificial Sequence
<220> FEATURE:
<223> OTHER INFORMATION: Mutagenesis primer TaqAYR-3

<400> SEQUENCE: 25
gctagctcct gggagaggcg gtaggccgac atgccgtaga gg                        42

<210> SEQ ID NO 26
<211> LENGTH: 45
<212> TYPE: DNA
<213> ORGANISM: Artificial Sequence
<220> FEATURE:
<223> OTHER INFORMATION: Mutagenesis primer TaqRRR-5

<400> SEQUENCE: 26
cccaggagct agccatccgt cgccgtgagg cccaggcctt cattg                     45

<210> SEQ ID NO 27
<211> LENGTH: 45
<212> TYPE: DNA
<213> ORGANISM: Artificial Sequence
<220> FEATURE:
<223> OTHER INFORMATION: Mutagenesis primer TaqRRR-3

<400> SEQUENCE: 27
caatgaaggc ctgggcctca cggcgacgga tggctagctc ctggg                     45

<210> SEQ ID NO 28
<211> LENGTH: 39
<212> TYPE: DNA
<213> ORGANISM: Artificial Sequence
<220> FEATURE:
<223> OTHER INFORMATION: Mutagenesis primer aa5

<400> SEQUENCE: 28
cgggtgaaga gcgtgcgggc ggcggccgag cgcatggcc                            39

<210> SEQ ID NO 29
<211> LENGTH: 39
<212> TYPE: DNA
<213> ORGANISM: Artificial Sequence
<220> FEATURE:
<223> OTHER INFORMATION: Mutagenesis primer aa3

<400> SEQUENCE: 29
ggccatgcgc tcggccgccg cccgcacgct cttcacccg                            39
```

<210> SEQ ID NO 30
<211> LENGTH: 42
<212> TYPE: DNA
<213> ORGANISM: Artificial Sequence
<220> FEATURE:
<223> OTHER INFORMATION: Mutagenesis primer TaqAYR-5

<400> SEQUENCE: 30
cctctacggc atgtcggcct accgcctctc ccaggagcta gc        42

<210> SEQ ID NO 31
<211> LENGTH: 42
<212> TYPE: DNA
<213> ORGANISM: Artificial Sequence
<220> FEATURE:
<223> OTHER INFORMATION: Mutagenesis primer TaqAYR-3

<400> SEQUENCE: 31
gctagctcct gggagaggcg gtaggccgac atgccgtaga gg        42

<210> SEQ ID NO 32
<211> LENGTH: 45
<212> TYPE: DNA
<213> ORGANISM: Artificial Sequence
<220> FEATURE:
<223> OTHER INFORMATION: Mutagenesis primer TaqRRR-5

<400> SEQUENCE: 32
cccaggagct agccatccgt cgccgtgagg cccaggcctt cattg     45

<210> SEQ ID NO 33
<211> LENGTH: 45
<212> TYPE: DNA
<213> ORGANISM: Artificial Sequence
<220> FEATURE:
<223> OTHER INFORMATION: Mutagenesis primer TaqRRR-3

<400> SEQUENCE: 33
caatgaaggc ctgggcctca cggcgacgga tggctagctc ctggg     45

<210> SEQ ID NO 34
<211> LENGTH: 39
<212> TYPE: DNA
<213> ORGANISM: Artificial Sequence
<220> FEATURE:
<223> OTHER INFORMATION: Mutagenesis primer ha5

<400> SEQUENCE: 34
cgggtgaaga gcgtgcggca tgcggccgag cgcatggcc           39

<210> SEQ ID NO 35
<211> LENGTH: 39
<212> TYPE: DNA
<213> ORGANISM: Artificial Sequence
<220> FEATURE:
<223> OTHER INFORMATION: Mutagenesis primer ha3

<400> SEQUENCE: 35
ggccatgcgc tcggccgcat gccgcacgct cttcacccg           39

<210> SEQ ID NO 36
<211> LENGTH: 39
<212> TYPE: DNA
<213> ORGANISM: Artificial Sequence
<220> FEATURE:
<223> OTHER INFORMATION: Mutagenesis primer hk5

<400> SEQUENCE: 36
cgggtgaaga gcgtgcggca taaagccgag cgcatggcc          39

<210> SEQ ID NO 37
<211> LENGTH: 39
<212> TYPE: DNA
<213> ORGANISM: Artificial Sequence
<220> FEATURE:
<223> OTHER INFORMATION: Mutagenesis primer hk3

<400> SEQUENCE: 37
ggccatgcgc tcggctttat gccgcacgct cttcacccg          39

<210> SEQ ID NO 38
<211> LENGTH: 39
<212> TYPE: DNA
<213> ORGANISM: Artificial Sequence
<220> FEATURE:
<223> OTHER INFORMATION: Mutagenesis primer rr5

<400> SEQUENCE: 38
cgggtgaaga gcgtgcggcg ccgcgccgag cgcatggcc          39

<210> SEQ ID NO 39
<211> LENGTH: 39
<212> TYPE: DNA
<213> ORGANISM: Artificial Sequence
<220> FEATURE:
<223> OTHER INFORMATION: Mutagenesis primer rr3

<400> SEQUENCE: 39
ggccatgcgc tcggcgcggc gccgcacgct cttcacccg          39

<210> SEQ ID NO 40
<211> LENGTH: 544
<212> TYPE: PRT
<213> ORGANISM: Artificial Sequence
<220> FEATURE:
<223> OTHER INFORMATION: Amino acid sequence of DNA polymerase variant
      Taq55

<400> SEQUENCE: 40

Met Ser Pro Lys Ala Leu Glu Glu Ala Pro Trp Pro Pro Glu Gly
1               5                   10                  15

Ala Phe Val Gly Phe Val Leu Ser Arg Lys Glu Pro Met Trp Ala Asp
            20                  25                  30

Leu Leu Ala Leu Ala Ala Ala Arg Gly Gly Arg Val His Arg Ala Pro
        35                  40                  45

Glu Pro Tyr Lys Ala Leu Arg Asp Leu Lys Glu Ala Arg Gly Leu Leu
    50                  55                  60

Ala Lys Asp Leu Ser Val Leu Ala Leu Arg Glu Gly Leu Gly Leu Pro
65                  70                  75                  80

Pro Gly Asp Asp Pro Met Leu Leu Ala Tyr Leu Leu Asp Pro Ser Asn
                85                  90                  95

Thr Thr Pro Glu Gly Val Ala Arg Arg Tyr Gly Gly Glu Trp Thr Glu
            100                 105                 110

Glu Ala Gly Glu Arg Ala Ala Leu Ser Glu Arg Leu Phe Ala Asn Leu
        115                 120                 125

Trp Gly Arg Leu Glu Gly Glu Glu Arg Leu Leu Trp Leu Tyr Arg Glu
    130                 135                 140

Val Glu Arg Pro Leu Ser Ala Val Leu Ala His Met Glu Ala Thr Gly 145                 150                 155                 160

Val Arg Leu Asp Val Ala Tyr Leu Arg Ala Leu Ser Leu Glu Val Ala
                    165                 170                 175

Glu Glu Ile Ala Arg Leu Glu Ala Glu Val Phe Arg Leu Ala Gly His
                    180                 185                 190

Pro Phe Asn Leu Asn Ser Arg Asp Gln Leu Glu Arg Val Leu Phe Asp
                    195                 200                 205

Glu Leu Gly Leu Pro Ala Ile Gly Lys Thr Glu Lys Thr Gly Lys Arg
        210                 215                 220

Ser Thr Ser Ala Ala Val Leu Glu Ala Leu Arg Glu Ala His Pro Ile
225                 230                 235                 240

Val Glu Lys Ile Leu Gln Tyr Arg Glu Leu Thr Lys Leu Lys Ser Thr
                    245                 250                 255

Tyr Ile Asp Pro Leu Pro Asp Leu Ile His Pro Arg Thr Gly Arg Leu
                    260                 265                 270

His Thr Arg Phe Asn Gln Thr Ala Thr Ala Thr Gly Arg Leu Ser Ser
                    275                 280                 285

Ser Asp Pro Asn Leu Gln Asn Ile Pro Val Arg Thr Pro Leu Gly Gln
        290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
                    325                 330                 335

Asp Glu Asn Leu Ile Arg Val Phe Gln Glu Gly Arg Asp Ile His Thr
                    340                 345                 350

Glu Thr Ala Ser Trp Met Phe Gly Val Pro Arg Glu Ala Val Asp Pro
                    355                 360                 365

Leu Met Arg Arg Ala Ala Lys Thr Ile Asn Phe Gly Val Leu Tyr Gly
        370                 375                 380

Met Ser Ala His Arg Leu Ser Gln Glu Leu Ala Ile Pro Tyr Ala Glu
385                 390                 395                 400

Ala Gln Ala Phe Ile Glu Arg Tyr Phe Gln Ser Phe Pro Lys Val Arg
                    405                 410                 415

Ala Trp Ile Glu Lys Thr Leu Glu Glu Gly Arg Arg Arg Gly Tyr Val
                    420                 425                 430

Glu Thr Leu Phe Gly Arg Arg Arg Tyr Val Pro Asp Leu Glu Ala Arg
                    435                 440                 445

Val Lys Ser Val Arg Glu Ala Ala Glu Arg Met Ala Phe Asn Met Pro
450                 455                 460

Val Gln Gly Thr Ala Ala Asp Leu Met Lys Leu Ala Met Val Lys Leu
465                 470                 475                 480

Phe Pro Arg Leu Glu Glu Met Gly Ala Arg Met Leu Leu Gln Val His
                    485                 490                 495

Asp Glu Leu Val Leu Glu Ala Pro Lys Glu Arg Ala Glu Ala Val Ala
                    500                 505                 510

Arg Leu Ala Lys Glu Val Met Glu Gly Val Tyr Pro Leu Ala Val Pro
                    515                 520                 525

Leu Glu Val Glu Val Gly Ile Gly Glu Asp Trp Leu Ser Ala Lys Glu
                    530                 535                 540

<210> SEQ ID NO 41
<211> LENGTH: 544
<212> TYPE: PRT
<213> ORGANISM: Artificial Sequence
<220> FEATURE:
<223> OTHER INFORMATION: Amino acid sequence of DNA polymerase variant Taq56

<400> SEQUENCE: 41

```
Met Ser Pro Lys Ala Leu Glu Glu Ala Pro Trp Pro Pro Glu Gly
1               5                   10                  15

Ala Phe Val Gly Phe Val Leu Ser Arg Lys Glu Pro Met Trp Ala Asp
            20                  25                  30

Leu Leu Ala Leu Ala Ala Arg Gly Gly Arg Val His Arg Ala Pro
        35                  40                  45

Glu Pro Tyr Lys Ala Leu Arg Asp Leu Lys Glu Ala Arg Gly Leu Leu
50                  55                  60

Ala Lys Asp Leu Ser Val Leu Ala Leu Arg Glu Gly Leu Gly Leu Pro
65                  70                  75                  80

Pro Gly Asp Asp Pro Met Leu Leu Ala Tyr Leu Leu Asp Pro Ser Asn
                85                  90                  95

Thr Thr Pro Glu Gly Val Ala Arg Arg Tyr Gly Gly Glu Trp Thr Glu
                100                 105                 110

Glu Ala Gly Glu Arg Ala Ala Leu Ser Glu Arg Leu Phe Ala Asn Leu
            115                 120                 125

Trp Gly Arg Leu Glu Gly Glu Glu Arg Leu Leu Trp Leu Tyr Arg Glu
        130                 135                 140

Val Glu Arg Pro Leu Ser Ala Val Leu Ala His Met Glu Ala Thr Gly
145                 150                 155                 160

Val Arg Leu Asp Val Ala Tyr Leu Arg Ala Leu Ser Leu Glu Val Ala
                165                 170                 175

Glu Glu Ile Ala Arg Leu Glu Ala Glu Val Phe Arg Leu Ala Gly His
                180                 185                 190

Pro Phe Asn Leu Asn Ser Arg Asp Gln Leu Glu Arg Val Leu Phe Asp
            195                 200                 205

Glu Leu Gly Leu Pro Ala Ile Gly Lys Thr Glu Lys Thr Gly Lys Arg
        210                 215                 220

Ser Thr Ser Ala Ala Val Leu Glu Ala Leu Arg Glu Ala His Pro Ile
225                 230                 235                 240

Val Glu Lys Ile Leu Gln Tyr Arg Glu Leu Thr Lys Leu Lys Ser Thr
                245                 250                 255

Tyr Ile Asp Pro Leu Pro Asp Leu Ile His Pro Arg Thr Gly Arg Leu
                260                 265                 270

His Thr Arg Phe Asn Gln Thr Ala Thr Ala Thr Gly Arg Leu Ser Ser
            275                 280                 285

Ser Asp Pro Asn Leu Gln Asn Ile Pro Val Arg Thr Pro Leu Gly Gln
        290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Arg Asp Ile His Thr
                340                 345                 350

Glu Thr Ala Ser Trp Met Phe Gly Val Pro Arg Glu Ala Val Asp Pro
            355                 360                 365

Leu Met Arg Arg Ala Ala Lys Thr Ile Asn Phe Gly Val Leu Tyr Gly
        370                 375                 380

Met Ser Ala His Arg Leu Ser Gln Glu Leu Ala Ile Pro Tyr Lys Glu
```

```
            385                 390                 395                 400
Ala Gln Ala Phe Ile Glu Arg Tyr Phe Gln Ser Phe Pro Lys Val Arg
                    405                 410                 415

Ala Trp Ile Glu Lys Thr Leu Glu Glu Gly Arg Arg Gly Tyr Val
                420                 425                 430

Glu Thr Leu Phe Gly Arg Arg Arg Tyr Val Pro Asp Leu Glu Ala Arg
                    435                 440                 445

Val Lys Ser Val Arg Glu Ala Ala Glu Arg Met Ala Phe Asn Met Pro
450                 455                 460

Val Gln Gly Thr Ala Ala Asp Leu Met Lys Leu Ala Met Val Lys Leu
465                 470                 475                 480

Phe Pro Arg Leu Glu Glu Met Gly Ala Arg Met Leu Leu Gln Val His
                485                 490                 495

Asp Glu Leu Val Leu Glu Ala Pro Lys Glu Arg Ala Glu Ala Val Ala
                500                 505                 510

Arg Leu Ala Lys Glu Val Met Glu Gly Val Tyr Pro Leu Ala Val Pro
            515                 520                 525

Leu Glu Val Glu Val Gly Ile Gly Glu Asp Trp Leu Ser Ala Lys Glu
            530                 535                 540

<210> SEQ ID NO 42
<211> LENGTH: 544
<212> TYPE: PRT
<213> ORGANISM: Artificial Sequence
<220> FEATURE:
<223> OTHER INFORMATION: Amino acid sequence of DNA polymerase variant
      Taq57

<400> SEQUENCE: 42

Met Ser Pro Lys Ala Leu Glu Glu Ala Pro Trp Pro Pro Glu Gly
1               5                   10                  15

Ala Phe Val Gly Phe Val Leu Ser Arg Lys Glu Pro Met Trp Ala Asp
                20                  25                  30

Leu Leu Ala Leu Ala Ala Ala Arg Gly Gly Arg Val His Arg Ala Pro
            35                  40                  45

Glu Pro Tyr Lys Ala Leu Arg Asp Leu Lys Glu Ala Arg Gly Leu Leu
        50                  55                  60

Ala Lys Asp Leu Ser Val Leu Ala Leu Arg Glu Gly Leu Gly Leu Pro
65                  70                  75                  80

Pro Gly Asp Asp Pro Met Leu Leu Ala Tyr Leu Leu Asp Pro Ser Asn
                85                  90                  95

Thr Thr Pro Glu Gly Val Ala Arg Arg Tyr Gly Gly Glu Trp Thr Glu
                100                 105                 110

Glu Ala Gly Glu Arg Ala Ala Leu Ser Glu Arg Leu Phe Ala Asn Leu
            115                 120                 125

Trp Gly Arg Leu Glu Gly Glu Glu Arg Leu Leu Trp Leu Tyr Arg Glu
        130                 135                 140

Val Glu Arg Pro Leu Ser Ala Val Leu Ala His Met Glu Ala Thr Gly
145                 150                 155                 160

Val Arg Leu Asp Val Ala Tyr Leu Arg Ala Leu Ser Leu Glu Val Ala
                165                 170                 175

Glu Glu Ile Ala Arg Leu Glu Ala Glu Val Phe Arg Leu Ala Gly His
                180                 185                 190

Pro Phe Asn Leu Asn Ser Arg Asp Gln Leu Glu Arg Val Leu Phe Asp
            195                 200                 205
```

Glu Leu Gly Leu Pro Ala Ile Gly Lys Thr Glu Lys Thr Gly Lys Arg
    210                 215                 220

Ser Thr Ser Ala Ala Val Leu Glu Ala Leu Arg Glu Ala His Pro Ile
225                 230                 235                 240

Val Glu Lys Ile Leu Gln Tyr Arg Glu Leu Thr Lys Leu Lys Ser Thr
                245                 250                 255

Tyr Ile Asp Pro Leu Pro Asp Leu Ile His Pro Arg Thr Gly Arg Leu
            260                 265                 270

His Thr Arg Phe Asn Gln Thr Ala Thr Ala Thr Gly Arg Leu Ser Ser
        275                 280                 285

Ser Asp Pro Asn Leu Gln Asn Ile Pro Val Arg Thr Pro Leu Gly Gln
290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Arg Asp Ile His Thr
            340                 345                 350

Glu Thr Ala Ser Trp Met Phe Gly Val Pro Arg Glu Ala Val Asp Pro
        355                 360                 365

Leu Met Arg Arg Ala Ala Lys Thr Ile Asn Phe Gly Val Leu Tyr Gly
370                 375                 380

Met Ser Ala His Arg Leu Ser Gln Glu Leu Ala Ile Pro Arg Lys Glu
385                 390                 395                 400

Ala Gln Ala Phe Ile Glu Arg Tyr Phe Gln Ser Phe Pro Lys Val Arg
                405                 410                 415

Ala Trp Ile Glu Lys Thr Leu Glu Glu Gly Arg Arg Arg Gly Tyr Val
            420                 425                 430

Glu Thr Leu Phe Gly Arg Arg Arg Tyr Val Pro Asp Leu Glu Ala Arg
        435                 440                 445

Val Lys Ser Val Arg Glu Ala Ala Glu Arg Met Ala Phe Asn Met Pro
450                 455                 460

Val Gln Gly Thr Ala Ala Asp Leu Met Lys Leu Ala Met Val Lys Leu
465                 470                 475                 480

Phe Pro Arg Leu Glu Glu Met Gly Ala Arg Met Leu Leu Gln Val His
                485                 490                 495

Asp Glu Leu Val Leu Glu Ala Pro Lys Glu Arg Ala Glu Ala Val Ala
            500                 505                 510

Arg Leu Ala Lys Glu Val Met Glu Gly Val Tyr Pro Leu Ala Val Pro
        515                 520                 525

Leu Glu Val Glu Val Gly Ile Gly Glu Asp Trp Leu Ser Ala Lys Glu
530                 535                 540

<210> SEQ ID NO 43
<211> LENGTH: 544
<212> TYPE: PRT
<213> ORGANISM: Artificial Sequence
<220> FEATURE:
<223> OTHER INFORMATION: Amino acid sequence of DNA polymerase variant
      Taq58

<400> SEQUENCE: 43

Met Ser Pro Lys Ala Leu Glu Glu Ala Pro Trp Pro Pro Glu Gly
1               5                   10                  15

Ala Phe Val Gly Phe Val Leu Ser Arg Lys Glu Pro Met Trp Ala Asp
            20                  25                  30

```
Leu Leu Ala Leu Ala Ala Ala Arg Gly Gly Arg Val His Arg Ala Pro
            35                  40                  45

Glu Pro Tyr Lys Ala Leu Arg Asp Leu Lys Glu Ala Arg Gly Leu Leu
 50                  55                  60

Ala Lys Asp Leu Ser Val Leu Ala Leu Arg Glu Gly Leu Gly Leu Pro
 65                  70                  75                  80

Pro Gly Asp Asp Pro Met Leu Leu Ala Tyr Leu Leu Asp Pro Ser Asn
                 85                  90                  95

Thr Thr Pro Glu Gly Val Ala Arg Arg Tyr Gly Gly Glu Trp Thr Glu
            100                 105                 110

Glu Ala Gly Glu Arg Ala Ala Leu Ser Glu Arg Leu Phe Ala Asn Leu
            115                 120                 125

Trp Gly Arg Leu Glu Gly Glu Glu Arg Leu Leu Trp Leu Tyr Arg Glu
130                 135                 140

Val Glu Arg Pro Leu Ser Ala Val Leu Ala His Met Glu Ala Thr Gly
145                 150                 155                 160

Val Arg Leu Asp Val Ala Tyr Leu Arg Ala Leu Ser Leu Glu Val Ala
                165                 170                 175

Glu Glu Ile Ala Arg Leu Glu Ala Glu Val Phe Arg Leu Ala Gly His
                180                 185                 190

Pro Phe Asn Leu Asn Ser Arg Asp Gln Leu Glu Arg Val Leu Phe Asp
            195                 200                 205

Glu Leu Gly Leu Pro Ala Ile Gly Lys Thr Glu Lys Thr Gly Lys Arg
            210                 215                 220

Ser Thr Ser Ala Ala Val Leu Glu Ala Leu Arg Glu Ala His Pro Ile
225                 230                 235                 240

Val Glu Lys Ile Leu Gln Tyr Arg Glu Leu Thr Lys Leu Lys Ser Thr
                245                 250                 255

Tyr Ile Asp Pro Leu Pro Asp Leu Ile His Pro Arg Thr Gly Arg Leu
                260                 265                 270

His Thr Arg Phe Asn Gln Thr Ala Thr Ala Thr Gly Arg Leu Ser Ser
            275                 280                 285

Ser Asp Pro Asn Leu Gln Asn Ile Pro Val Arg Thr Pro Leu Gly Gln
290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Arg Asp Ile His Thr
            340                 345                 350

Glu Thr Ala Ser Trp Met Phe Gly Val Pro Arg Glu Ala Val Asp Pro
            355                 360                 365

Leu Met Arg Arg Ala Ala Lys Thr Ile Asn Phe Gly Val Leu Tyr Gly
370                 375                 380

Met Ser Ala His Arg Leu Ser Gln Glu Leu Ala Ile Ser Arg Lys Glu
385                 390                 395                 400

Ala Gln Ala Phe Ile Glu Arg Tyr Phe Gln Ser Phe Pro Lys Val Arg
                405                 410                 415

Ala Trp Ile Glu Lys Thr Leu Glu Glu Gly Arg Arg Arg Gly Tyr Val
            420                 425                 430

Glu Thr Leu Phe Gly Arg Arg Arg Tyr Val Pro Asp Leu Glu Ala Arg
            435                 440                 445
```

```
Val Lys Ser Val Arg Glu Ala Ala Glu Arg Met Ala Phe Asn Met Pro
450                 455                 460
Val Gln Gly Thr Ala Ala Asp Leu Met Lys Leu Ala Met Val Lys Leu
465                 470                 475                 480
Phe Pro Arg Leu Glu Glu Met Gly Ala Arg Met Leu Leu Gln Val His
                485                 490                 495
Asp Glu Leu Val Leu Glu Ala Pro Lys Glu Arg Ala Glu Ala Val Ala
            500                 505                 510
Arg Leu Ala Lys Glu Val Met Glu Gly Val Tyr Pro Leu Ala Val Pro
        515                 520                 525
Leu Glu Val Glu Val Gly Ile Gly Glu Asp Trp Leu Ser Ala Lys Glu
    530                 535                 540

<210> SEQ ID NO 44
<211> LENGTH: 544
<212> TYPE: PRT
<213> ORGANISM: Artificial Sequence
<220> FEATURE:
<223> OTHER INFORMATION: Amino acid sequence of DNA polymerase variant
      Taq59

<400> SEQUENCE: 44

Met Ser Pro Lys Ala Leu Glu Glu Ala Pro Trp Pro Pro Glu Gly
1               5                   10                  15
Ala Phe Val Gly Phe Val Leu Ser Arg Lys Glu Pro Met Trp Ala Asp
                20                  25                  30
Leu Leu Ala Leu Ala Ala Ala Arg Gly Gly Arg Val His Arg Ala Pro
            35                  40                  45
Glu Pro Tyr Lys Ala Leu Arg Asp Leu Lys Glu Ala Arg Gly Leu Leu
        50                  55                  60
Ala Lys Asp Leu Ser Val Leu Ala Leu Arg Glu Gly Leu Gly Leu Pro
65                  70                  75                  80
Pro Gly Asp Asp Pro Met Leu Leu Ala Tyr Leu Leu Asp Pro Ser Asn
                85                  90                  95
Thr Thr Pro Glu Gly Val Ala Arg Arg Tyr Gly Gly Glu Trp Thr Glu
            100                 105                 110
Glu Ala Gly Glu Arg Ala Ala Leu Ser Glu Arg Leu Phe Ala Asn Leu
        115                 120                 125
Trp Gly Arg Leu Glu Gly Glu Glu Arg Leu Leu Trp Leu Tyr Arg Glu
    130                 135                 140
Val Glu Arg Pro Leu Ser Ala Val Leu Ala His Met Glu Ala Thr Gly
145                 150                 155                 160
Val Arg Leu Asp Val Ala Tyr Leu Arg Ala Leu Ser Leu Glu Val Ala
                165                 170                 175
Glu Glu Ile Ala Arg Leu Glu Ala Glu Val Phe Arg Leu Ala Gly His
            180                 185                 190
Pro Phe Asn Leu Asn Ser Arg Asp Gln Leu Glu Arg Val Leu Phe Asp
        195                 200                 205
Glu Leu Gly Leu Pro Ala Ile Gly Lys Thr Glu Lys Thr Gly Lys Arg
    210                 215                 220
Ser Thr Ser Ala Ala Val Leu Glu Ala Leu Arg Glu Ala His Pro Ile
225                 230                 235                 240
Val Glu Lys Ile Leu Gln Tyr Arg Glu Leu Thr Lys Leu Lys Ser Thr
                245                 250                 255
Tyr Ile Asp Pro Leu Pro Asp Leu Ile His Pro Arg Thr Gly Arg Leu
            260                 265                 270
```

His Thr Arg Phe Asn Gln Thr Ala Thr Ala Thr Gly Arg Leu Ser Ser
            275                 280                 285

Ser Asp Pro Asn Leu Gln Asn Ile Pro Val Arg Thr Pro Leu Gly Gln
        290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Arg Asp Ile His Thr
            340                 345                 350

Glu Thr Ala Ser Trp Met Phe Gly Val Pro Arg Glu Ala Val Asp Pro
        355                 360                 365

Leu Met Arg Arg Ala Ala Lys Thr Ile Asn Phe Gly Val Leu Tyr Gly
370                 375                 380

Met Ser Ala His Arg Leu Ser Gln Glu Leu Ala Ile Arg Arg Arg Glu
385                 390                 395                 400

Ala Gln Ala Phe Ile Glu Arg Tyr Phe Gln Ser Phe Pro Lys Val Arg
                405                 410                 415

Ala Trp Ile Glu Lys Thr Leu Glu Glu Gly Arg Arg Arg Gly Tyr Val
            420                 425                 430

Glu Thr Leu Phe Gly Arg Arg Arg Tyr Val Pro Asp Leu Glu Ala Arg
        435                 440                 445

Val Lys Ser Val Arg Glu Ala Ala Glu Arg Met Ala Phe Asn Met Pro
450                 455                 460

Val Gln Gly Thr Ala Ala Asp Leu Met Lys Leu Ala Met Val Lys Leu
465                 470                 475                 480

Phe Pro Arg Leu Glu Glu Met Gly Ala Arg Met Leu Leu Gln Val His
                485                 490                 495

Asp Glu Leu Val Leu Glu Ala Pro Lys Glu Arg Ala Glu Ala Val Ala
            500                 505                 510

Arg Leu Ala Lys Glu Val Met Glu Gly Val Tyr Pro Leu Ala Val Pro
        515                 520                 525

Leu Glu Val Glu Val Gly Ile Gly Glu Asp Trp Leu Ser Ala Lys Glu
530                 535                 540

<210> SEQ ID NO 45
<211> LENGTH: 544
<212> TYPE: PRT
<213> ORGANISM: Artificial Sequence
<220> FEATURE:
<223> OTHER INFORMATION: Amino acid sequence of DNA polymerase variant
      Taq62

<400> SEQUENCE: 45

Met Ser Pro Lys Ala Leu Glu Glu Ala Pro Trp Pro Pro Glu Gly
1               5                   10                  15

Ala Phe Val Gly Phe Val Leu Ser Arg Lys Glu Pro Met Trp Ala Asp
            20                  25                  30

Leu Leu Ala Leu Ala Ala Ala Arg Gly Gly Arg Val His Arg Ala Pro
        35                  40                  45

Glu Pro Tyr Lys Ala Leu Arg Asp Leu Lys Glu Ala Arg Gly Leu Leu
    50                  55                  60

Ala Lys Asp Leu Ser Val Leu Ala Leu Arg Glu Gly Leu Gly Leu Pro
65                  70                  75                  80

Pro Gly Asp Asp Pro Met Leu Leu Ala Tyr Leu Leu Asp Pro Ser Asn

```
                           85                  90                  95
Thr Thr Pro Glu Gly Val Ala Arg Arg Tyr Gly Gly Glu Trp Thr Glu
                100                 105                 110

Glu Ala Gly Glu Arg Ala Ala Leu Ser Glu Arg Leu Phe Ala Asn Leu
            115                 120                 125

Trp Gly Arg Leu Glu Gly Glu Arg Leu Leu Trp Leu Tyr Arg Glu
        130                 135                 140

Val Glu Arg Pro Leu Ser Ala Val Leu Ala His Met Glu Ala Thr Gly
145                 150                 155                 160

Val Arg Leu Asp Val Ala Tyr Leu Arg Ala Leu Ser Leu Glu Val Ala
                165                 170                 175

Glu Glu Ile Ala Arg Leu Glu Ala Glu Val Phe Arg Leu Ala Gly His
                180                 185                 190

Pro Phe Asn Leu Asn Ser Arg Asp Gln Leu Glu Arg Val Leu Phe Asp
                195                 200                 205

Glu Leu Gly Leu Pro Ala Ile Gly Lys Thr Glu Lys Thr Gly Lys Arg
            210                 215                 220

Ser Thr Ser Ala Ala Val Leu Glu Ala Leu Arg Glu Ala His Pro Ile
225                 230                 235                 240

Val Glu Lys Ile Leu Gln Tyr Arg Glu Leu Thr Lys Leu Lys Ser Thr
                245                 250                 255

Tyr Ile Asp Pro Leu Pro Asp Leu Ile His Pro Arg Thr Gly Arg Leu
                260                 265                 270

His Thr Arg Phe Asn Gln Thr Ala Thr Ala Thr Gly Arg Leu Ser Ser
            275                 280                 285

Ser Asp Pro Asn Leu Gln Asn Ile Pro Val Arg Thr Pro Leu Gly Gln
290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Arg Asp Ile His Thr
                340                 345                 350

Glu Thr Ala Ser Trp Met Phe Gly Val Pro Arg Glu Ala Val Asp Pro
            355                 360                 365

Leu Met Arg Arg Ala Ala Lys Thr Ile Asn Phe Gly Val Leu Tyr Gly
            370                 375                 380

Met Ser Ala Tyr Arg Leu Ser Gln Glu Leu Ala Ile Arg Arg Arg Glu
385                 390                 395                 400

Ala Gln Ala Phe Ile Glu Arg Tyr Phe Gln Ser Phe Pro Lys Val Arg
                405                 410                 415

Ala Trp Ile Glu Lys Thr Leu Glu Glu Gly Arg Arg Arg Gly Tyr Val
                420                 425                 430

Glu Thr Leu Phe Gly Arg Arg Arg Tyr Val Pro Asp Leu Glu Ala Arg
            435                 440                 445

Val Lys Ser Val Arg Ala Ala Ala Glu Arg Met Ala Phe Asn Met Pro
            450                 455                 460

Val Gln Gly Thr Ala Ala Asp Leu Met Lys Leu Ala Met Val Lys Leu
465                 470                 475                 480

Phe Pro Arg Leu Glu Glu Met Gly Ala Arg Met Leu Leu Gln Val His
                485                 490                 495

Asp Glu Leu Val Leu Glu Ala Pro Lys Glu Arg Ala Glu Ala Val Ala
                500                 505                 510
```

```
Arg Leu Ala Lys Glu Val Met Glu Gly Val Tyr Pro Leu Ala Val Pro
        515                 520                 525

Leu Glu Val Glu Val Gly Ile Gly Glu Asp Trp Leu Ser Ala Lys Glu
    530                 535                 540
```

<210> SEQ ID NO 46
<211> LENGTH: 544
<212> TYPE: PRT
<213> ORGANISM: Artificial Sequence
<220> FEATURE:
<223> OTHER INFORMATION: Amino acid sequence of DNA polymerase variant Taq63

<400> SEQUENCE: 46

```
Met Ser Pro Lys Ala Leu Glu Glu Ala Pro Trp Pro Pro Glu Gly
1               5                   10                  15

Ala Phe Val Gly Phe Val Leu Ser Arg Lys Glu Pro Met Trp Ala Asp
            20                  25                  30

Leu Leu Ala Leu Ala Ala Ala Arg Gly Gly Arg Val His Arg Ala Pro
        35                  40                  45

Glu Pro Tyr Lys Ala Leu Arg Asp Leu Lys Glu Ala Arg Gly Leu Leu
    50                  55                  60

Ala Lys Asp Leu Ser Val Leu Ala Leu Arg Glu Gly Leu Gly Leu Pro
65                  70                  75                  80

Pro Gly Asp Asp Pro Met Leu Leu Ala Tyr Leu Leu Asp Pro Ser Asn
                85                  90                  95

Thr Thr Pro Glu Gly Val Ala Arg Arg Tyr Gly Gly Glu Trp Thr Glu
            100                 105                 110

Glu Ala Gly Glu Arg Ala Ala Leu Ser Glu Arg Leu Phe Ala Asn Leu
        115                 120                 125

Trp Gly Arg Leu Glu Gly Glu Glu Arg Leu Leu Trp Leu Tyr Arg Glu
    130                 135                 140

Val Glu Arg Pro Leu Ser Ala Val Leu Ala His Met Glu Ala Thr Gly
145                 150                 155                 160

Val Arg Leu Asp Val Ala Tyr Leu Arg Ala Leu Ser Leu Glu Val Ala
                165                 170                 175

Glu Glu Ile Ala Arg Leu Glu Ala Glu Val Phe Arg Leu Ala Gly His
            180                 185                 190

Pro Phe Asn Leu Asn Ser Arg Asp Gln Leu Glu Arg Val Leu Phe Asp
        195                 200                 205

Glu Leu Gly Leu Pro Ala Ile Gly Lys Thr Glu Lys Thr Gly Lys Arg
    210                 215                 220

Ser Thr Ser Ala Ala Val Leu Glu Ala Leu Arg Glu Ala His Pro Ile
225                 230                 235                 240

Val Glu Lys Ile Leu Gln Tyr Arg Glu Leu Thr Lys Leu Lys Ser Thr
                245                 250                 255

Tyr Ile Asp Pro Leu Pro Asp Leu Ile His Pro Arg Thr Gly Arg Leu
            260                 265                 270

His Thr Arg Phe Asn Gln Thr Ala Thr Ala Thr Gly Arg Leu Ser Ser
        275                 280                 285

Ser Asp Pro Asn Leu Gln Asn Ile Pro Val Arg Thr Pro Leu Gly Gln
    290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
```

325                 330                 335
Asp Glu Asn Leu Ile Arg Val Phe Gln Glu Gly Arg Asp Ile His Thr
                340                 345                 350
Glu Thr Ala Ser Trp Met Phe Gly Val Pro Arg Glu Ala Val Asp Pro
            355                 360                 365
Leu Met Arg Arg Ala Ala Lys Thr Ile Asn Phe Gly Val Leu Tyr Gly
        370                 375                 380
Met Ser Ala Tyr Arg Leu Ser Gln Glu Leu Ala Ile Arg Arg Arg Glu
385                 390                 395                 400
Ala Gln Ala Phe Ile Glu Arg Tyr Phe Gln Ser Phe Pro Lys Val Arg
                405                 410                 415
Ala Trp Ile Glu Lys Thr Leu Glu Glu Gly Arg Arg Arg Gly Tyr Val
                420                 425                 430
Glu Thr Leu Phe Gly Arg Arg Arg Tyr Val Pro Asp Leu Glu Ala Arg
            435                 440                 445
Val Lys Ser Val Arg His Ala Ala Glu Arg Met Ala Phe Asn Met Pro
450                 455                 460
Val Gln Gly Thr Ala Ala Asp Leu Met Lys Leu Ala Met Val Lys Leu
465                 470                 475                 480
Phe Pro Arg Leu Glu Glu Met Gly Ala Arg Met Leu Leu Gln Val His
                485                 490                 495
Asp Glu Leu Val Leu Glu Ala Pro Lys Glu Arg Ala Glu Ala Val Ala
                500                 505                 510
Arg Leu Ala Lys Glu Val Met Glu Gly Val Tyr Pro Leu Ala Val Pro
            515                 520                 525
Leu Glu Val Glu Val Gly Ile Gly Glu Asp Trp Leu Ser Ala Lys Glu
        530                 535                 540

<210> SEQ ID NO 47
<211> LENGTH: 544
<212> TYPE: PRT
<213> ORGANISM: Artificial Sequence
<220> FEATURE:
<223> OTHER INFORMATION: Amino acid sequence of DNA polymerase variant
      Taq64

<400> SEQUENCE: 47

Met Ser Pro Lys Ala Leu Glu Glu Ala Pro Trp Pro Pro Pro Glu Gly
1               5                   10                  15
Ala Phe Val Gly Phe Val Leu Ser Arg Lys Glu Pro Met Trp Ala Asp
                20                  25                  30
Leu Leu Ala Leu Ala Ala Ala Arg Gly Gly Arg Val His Arg Ala Pro
            35                  40                  45
Glu Pro Tyr Lys Ala Leu Arg Asp Leu Lys Glu Ala Arg Gly Leu Leu
        50                  55                  60
Ala Lys Asp Leu Ser Val Leu Ala Leu Arg Glu Gly Leu Gly Leu Pro
65                  70                  75                  80
Pro Gly Asp Asp Pro Met Leu Leu Ala Tyr Leu Leu Asp Pro Ser Asn
                85                  90                  95
Thr Thr Pro Glu Gly Val Ala Arg Arg Tyr Gly Gly Glu Trp Thr Glu
            100                 105                 110
Glu Ala Gly Glu Arg Ala Ala Leu Ser Glu Arg Leu Phe Ala Asn Leu
        115                 120                 125
Trp Gly Arg Leu Glu Gly Glu Glu Arg Leu Leu Trp Leu Tyr Arg Glu
    130                 135                 140

Val Glu Arg Pro Leu Ser Ala Val Leu Ala His Met Glu Ala Thr Gly
145                 150                 155                 160

Val Arg Leu Asp Val Ala Tyr Leu Arg Ala Leu Ser Leu Glu Val Ala
            165                 170                 175

Glu Glu Ile Ala Arg Leu Glu Ala Glu Val Phe Arg Leu Ala Gly His
        180                 185                 190

Pro Phe Asn Leu Asn Ser Arg Asp Gln Leu Glu Arg Val Leu Phe Asp
    195                 200                 205

Glu Leu Gly Leu Pro Ala Ile Gly Lys Thr Glu Lys Thr Gly Lys Arg
210                 215                 220

Ser Thr Ser Ala Ala Val Leu Glu Ala Leu Arg Glu Ala His Pro Ile
225                 230                 235                 240

Val Glu Lys Ile Leu Gln Tyr Arg Glu Leu Thr Lys Leu Lys Ser Thr
            245                 250                 255

Tyr Ile Asp Pro Leu Pro Asp Leu Ile His Pro Arg Thr Gly Arg Leu
        260                 265                 270

His Thr Arg Phe Asn Gln Thr Ala Thr Ala Thr Gly Arg Leu Ser Ser
    275                 280                 285

Ser Asp Pro Asn Leu Gln Asn Ile Pro Val Arg Thr Pro Leu Gly Gln
290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
            325                 330                 335

Asp Glu Asn Leu Ile Arg Val Phe Gln Glu Gly Arg Asp Ile His Thr
        340                 345                 350

Glu Thr Ala Ser Trp Met Phe Gly Val Pro Arg Glu Ala Val Asp Pro
    355                 360                 365

Leu Met Arg Arg Ala Ala Lys Thr Ile Asn Phe Gly Val Leu Tyr Gly
370                 375                 380

Met Ser Ala Tyr Arg Leu Ser Gln Glu Leu Ala Ile Arg Arg Arg Glu
385                 390                 395                 400

Ala Gln Ala Phe Ile Glu Arg Tyr Phe Gln Ser Phe Pro Lys Val Arg
            405                 410                 415

Ala Trp Ile Glu Lys Thr Leu Glu Glu Gly Arg Arg Arg Gly Tyr Val
        420                 425                 430

Glu Thr Leu Phe Gly Arg Arg Arg Tyr Val Pro Asp Leu Glu Ala Arg
    435                 440                 445

Val Lys Ser Val Arg His Lys Ala Glu Arg Met Ala Phe Asn Met Pro
450                 455                 460

Val Gln Gly Thr Ala Ala Asp Leu Met Lys Leu Ala Met Val Lys Leu
465                 470                 475                 480

Phe Pro Arg Leu Glu Glu Met Gly Ala Arg Met Leu Leu Gln Val His
            485                 490                 495

Asp Glu Leu Val Leu Glu Ala Pro Lys Glu Arg Ala Glu Ala Val Ala
        500                 505                 510

Arg Leu Ala Lys Glu Val Met Glu Gly Val Tyr Pro Leu Ala Val Pro
    515                 520                 525

Leu Glu Val Glu Val Gly Ile Gly Glu Asp Trp Leu Ser Ala Lys Glu
530                 535                 540

<210> SEQ ID NO 48
<211> LENGTH: 544
<212> TYPE: PRT

<213> ORGANISM: Artificial Sequence
<220> FEATURE:
<223> OTHER INFORMATION: Amino acid sequence of DNA polymerase variant Taq65

<400> SEQUENCE: 48

```
Met Ser Pro Lys Ala Leu Glu Glu Ala Pro Trp Pro Pro Glu Gly
1               5                   10                  15

Ala Phe Val Gly Phe Val Leu Ser Arg Lys Glu Pro Met Trp Ala Asp
            20                  25                  30

Leu Leu Ala Leu Ala Ala Arg Gly Gly Arg Val His Arg Ala Pro
        35                  40                  45

Glu Pro Tyr Lys Ala Leu Arg Asp Leu Lys Glu Ala Arg Gly Leu Leu
    50                  55                  60

Ala Lys Asp Leu Ser Val Leu Ala Leu Arg Glu Gly Leu Gly Leu Pro
65                  70                  75                  80

Pro Gly Asp Asp Pro Met Leu Leu Ala Tyr Leu Leu Asp Pro Ser Asn
                85                  90                  95

Thr Thr Pro Glu Gly Val Ala Arg Arg Tyr Gly Gly Glu Trp Thr Glu
                100                 105                 110

Glu Ala Gly Glu Arg Ala Ala Leu Ser Glu Arg Leu Phe Ala Asn Leu
            115                 120                 125

Trp Gly Arg Leu Glu Gly Glu Glu Arg Leu Leu Trp Leu Tyr Arg Glu
        130                 135                 140

Val Glu Arg Pro Leu Ser Ala Val Leu Ala His Met Glu Ala Thr Gly
145                 150                 155                 160

Val Arg Leu Asp Val Ala Tyr Leu Arg Ala Leu Ser Leu Glu Val Ala
                165                 170                 175

Glu Glu Ile Ala Arg Leu Glu Ala Glu Val Phe Arg Leu Ala Gly His
            180                 185                 190

Pro Phe Asn Leu Asn Ser Arg Asp Gln Leu Glu Arg Val Leu Phe Asp
        195                 200                 205

Glu Leu Gly Leu Pro Ala Ile Gly Lys Thr Glu Lys Thr Gly Lys Arg
    210                 215                 220

Ser Thr Ser Ala Ala Val Leu Glu Ala Leu Arg Glu Ala His Pro Ile
225                 230                 235                 240

Val Glu Lys Ile Leu Gln Tyr Arg Glu Leu Thr Lys Leu Lys Ser Thr
                245                 250                 255

Tyr Ile Asp Pro Leu Pro Asp Leu Ile His Pro Arg Thr Gly Arg Leu
            260                 265                 270

His Thr Arg Phe Asn Gln Thr Ala Thr Ala Thr Gly Arg Leu Ser Ser
        275                 280                 285

Ser Asp Pro Asn Leu Gln Asn Ile Pro Val Arg Thr Pro Leu Gly Gln
    290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Arg Asp Ile His Thr
            340                 345                 350

Glu Thr Ala Ser Trp Met Phe Gly Val Pro Arg Glu Ala Val Asp Pro
        355                 360                 365

Leu Met Arg Arg Ala Ala Lys Thr Ile Asn Phe Gly Val Leu Tyr Gly
    370                 375                 380
```

```
Met Ser Ala Tyr Arg Leu Ser Gln Glu Leu Ala Ile Arg Arg Arg Glu
385                 390                 395                 400

Ala Gln Ala Phe Ile Glu Arg Tyr Phe Gln Ser Phe Pro Lys Val Arg
            405                 410                 415

Ala Trp Ile Glu Lys Thr Leu Glu Glu Gly Arg Arg Arg Gly Tyr Val
            420                 425                 430

Glu Thr Leu Phe Gly Arg Arg Tyr Val Pro Asp Leu Glu Ala Arg
            435                 440                 445

Val Lys Ser Val Arg Arg Ala Glu Arg Met Ala Phe Asn Met Pro
450                 455                 460

Val Gln Gly Thr Ala Ala Asp Leu Met Lys Leu Ala Met Val Lys Leu
465                 470                 475                 480

Phe Pro Arg Leu Glu Glu Met Gly Ala Arg Met Leu Leu Gln Val His
            485                 490                 495

Asp Glu Leu Val Leu Glu Ala Pro Lys Glu Arg Ala Glu Ala Val Ala
            500                 505                 510

Arg Leu Ala Lys Glu Val Met Glu Gly Val Tyr Pro Leu Ala Val Pro
            515                 520                 525

Leu Glu Val Glu Val Gly Ile Gly Glu Asp Trp Leu Ser Ala Lys Glu
530                 535                 540

<210> SEQ ID NO 49
<211> LENGTH: 55
<212> TYPE: DNA
<213> ORGANISM: Artificial Sequence
<220> FEATURE:
<223> OTHER INFORMATION: 55nt Oligonuleotides M13-pri55

<400> SEQUENCE: 49
tcgtaatcat ggtcatagct gtttcctgtg tgaaattgtt atccgctcac aattc     55

<210> SEQ ID NO 50
<211> LENGTH: 27
<212> TYPE: DNA
<213> ORGANISM: Artificial Sequence
<220> FEATURE:
<223> OTHER INFORMATION: 27nt Oligonuleotides d27

<400> SEQUENCE: 50
agctatgacc atgattacga attgctt                                    27

<210> SEQ ID NO 51
<211> LENGTH: 49
<212> TYPE: DNA
<213> ORGANISM: Artificial Sequence
<220> FEATURE:
<223> OTHER INFORMATION: 49nt Oligonuleotides 49N

<400> SEQUENCE: 51
agctaccatg cctgcacgaa ttaagcaatt cgtaatcatg gtcatagct            49

<210> SEQ ID NO 52
<211> LENGTH: 11
<212> TYPE: PRT
<213> ORGANISM: Artificial Sequence
<220> FEATURE:
<223> OTHER INFORMATION: Amino acid sequence of Pyrococcus furiosus
      RFC-L PIP-box
```

-continued

```
<400> SEQUENCE: 52

Lys Gln Ala Thr Leu Phe Asp Phe Leu Lys Lys
1               5                   10
```